(12) United States Patent
King et al.

(10) Patent No.: US 8,378,066 B2
(45) Date of Patent: Feb. 19, 2013

(54) INSULINOTROPIC PEPTIDE SYNTHESIS USING SOLID AND SOLUTION PHASE COMBINATION TECHNIQUES

(75) Inventors: Barry Thomas King, Boulder, CO (US); Paul Adam Bury, Thornton, CO (US); Richard A. Gabel, Louisville, CO (US); John Edward Crider, Boulder, CO (US); Robert Thad Carr, II, Effingham, SC (US); Bradley S. DeHoff, Longmont, CO (US)

(73) Assignee: Corden Pharma Colorado, Inc., Boulder, CO (US)

( * ) Notice: Subject to any disclaimer, the term of this patent is extended or adjusted under 35 U.S.C. 154(b) by 678 days.

(21) Appl. No.: 12/288,934

(22) Filed: Oct. 24, 2008

(65) Prior Publication Data

US 2009/0149628 A1 Jun. 11, 2009

Related U.S. Application Data

(60) Provisional application No. 61/000,622, filed on Oct. 27, 2007.

(51) Int. Cl.
*C07K 7/06* (2006.01)
*C07K 7/08* (2006.01)
*C07K 14/46* (2006.01)
*C07K 14/605* (2006.01)

(52) U.S. Cl. ........ 530/324; 530/326; 530/327; 530/328; 530/332; 530/339; 530/345

(58) Field of Classification Search .................. None
See application file for complete search history.

(56) References Cited

U.S. PATENT DOCUMENTS

| | | | |
|---|---|---|---|
| 5,424,286 A | 6/1995 | Eng | |
| 6,015,881 A | 1/2000 | Kang et al. | |
| 6,329,336 B1 | 12/2001 | Bridon et al. | |
| 6,703,365 B2 | 3/2004 | Galloway et al. | |
| 6,887,849 B2 | 5/2005 | Bridon et al. | |
| 2005/0164912 A1 | 7/2005 | Bigelow et al. | |
| 2006/0135426 A1* | 6/2006 | Bridon et al. | 514/12 |

FOREIGN PATENT DOCUMENTS

| | | |
|---|---|---|
| EP | 1137667 | 11/2004 |
| WO | WO 00/34331 | 6/2000 |
| WO | WO 01/04156 | 1/2001 |
| WO | WO 2004/094461 | 11/2004 |
| WO | WO 2007/090496 | 8/2007 |
| WO | WO 2007/147816 | 12/2007 |

OTHER PUBLICATIONS

Liu et al. Orthogonal Ligation of Unprotected Peptide Segments through Pseudoproline Formation . . . Journal of the American Chemical Society. 1996, vol. 118, No. 2, pp. 307-312.*

International Search Report for the corresponding International Patent Application No. PCT/EP2008/064043, completed Feb. 19, 2009 (6 pgs).

A. Abedini and D. P. Raleigh, "Incorporation of Pseudoproline Derivatives Allows the Facile Synthesis of Human IAPP, a Highly Amyloidogenic and Aggregation-Prone Polypeptide," Organic Letters, (2005), vol. 7, No. 4, pp. 693-696.

Andersson, et al., "Large-Scale Synthesis of Peptides," Biopolymers (Peptide Science), (2000), vol. 55, pp. 227-250.

Coin, et al., "Solid-phase peptide synthesis: from standard procedures to the synthesis of difficult sequences," Nature Protocols, (2007), vol. 2, No. 12, pp. 3247-3256.

Cremer, et al., "Combining a polar resin and a pseudo-proline to optimize the solid-phase synthesis of a 'difficult sequence'," Journal of Peptide Science, (2006), 12:437-442.

Garcia-Martin, et al., "The Synergy of ChemMatrix Resin® and Pseudoproline Building Blocks Renders RANTES, a Complex Aggregated Chemokine*," Biopolymers (Peptide Science), (2006), vol. 84, pp. 566-575.

Sampson, et al., "The Synthesis of 'Difficult' Peptides Using 2-Hydroxy-4-Methoxybenzyl or Pseudoproline Amino Acid Building Blocks: a Comparative Study," Journal of Peptide Science, (1999), 5: 403-409.

Sélambarom, et al., "A Novel Route to Pseudoproline ($\Psi^{H,H}$ Pro)-Containing Dipeptides Building Blocks," International Journal of Peptide Research and Therapeutics, (Dec. 2005), vol. 11, No. 4, pp. 267-270.

Wöhr, et al., "Pseudo-Prolines as a Solubilizing, Structure-Disrupting Protection Technique in Peptide Synthesis," J. Am. Chem. Soc., (1996), 118, 9218-9227.

Mergler, et al., "Peptide Synthesis by a Combination of Solid-Phase and Solution Methods II[1] Synthesis of Fully Protected Peptide Fragments on 2-Methoxy-4-Alkoxy-Benzyl Alcohol Resin," Tetrahedron Letters, (1988), vol. 29, No. 32, pp. 4009-4012.

B. Kamber and B. Riniker, "The solid phase synthesis of protected peptides combined with fragment coupling in solution," Chemistry and Biology, ESCOM, (1992), pp. 525-526.

Riniker, et al., "A General Strategy for the Synthesis of Large Peptides: The Combined Solid-Phase and Solution Approach," Tetrahedron, (1993), vol. 49, No. 41, pp. 9307-9320.

Lloyd-Williams, et al., "Convergent Solid-Phase Peptide Synthesis," Tetrahedron, (1993), vol. 49, No. 48, pp. 11065-11133.

(Continued)

*Primary Examiner* — Jeffrey E Russel
(74) *Attorney, Agent, or Firm* — Faegre Baker Daniels LLP

(57) ABSTRACT

The present invention relates to the preparation of insulinotropic peptides that are synthesized using a solid and solution phase ("hybrid") approach. Generally, the approach includes synthesizing three different peptide intermediate fragments using solid phase chemistry. Solution phase chemistry is then used to add additional amino acid material to one of the fragments. The fragments are then coupled together in the solution phase. The use of a pseudoproline in one of the fragments eases solid phase synthesis of that fragment and also eases subsequent solution phase coupling of this fragment to other fragments. The present invention is very useful for forming insulinotropic peptides such as Exenatide(1-39) and its natural and non-natural counterparts.

55 Claims, 1 Drawing Sheet

OTHER PUBLICATIONS

Albericio, et al., "New Trends in Peptide Coupling Reagents," Organic Preparation and Procedures Int., (2001), 33 (3), pp. 203-303.

Novabiochem® Innovations 1/04, "Guidelines for the use of Pseudoproline Dipeptides," EMD Biosciences, (2004), 2 pgs.

Novabiochem® Innovations 3/04, "Synthesis design using pseudoproline dipeptides," EMD Biosciences, (2004), 4 pgs.

Svetlana Mojsov, "Glucagon-like Peptide-1 (GLP-1) and the Control of Glucose Metabolism in Mammals and Teleost Fish[1]," Amer. Zool., (2000), 40:246-258.

Drucker, Daniel J., "Glucagon-Like Peptides," Diabetes a Journal of the American Diabetes Association, (Feb. 1998), vol. 47(2), pp. 159-169.

Nyfeler, Rolf, "Peptide Synthesis via Fragment Condensation," Methods in Molecular Biology, (1994), vol. 35, pp. 303-316.

White, et al., "Pseudoproline dipeptides in Fmoc-solid phase peptide synthesis," Novabiochem® Merck Biosciences, from European Peptide Symposium Prague, (2004), 1 pg.

Mergler, et al., "Peptide Synthesis by a Combination of Solid-Phase and Solution Methods I: A New Very Acid-Labile Anchor Group for the Solid Phase Synthesis of Fully Protected Fragments[1])," Tetrahedron Letters, (1988), vol. 29, No. 32, pp. 4005-4008.

Barlose, et al., "Darstellung Geschutzter Peptid-Fragmente Unter Einsatz Substituierter Triphenylmethyl-Harze," Tetrahedron Letters, (1989), vol. 30, No. 30, pp. 3943-3946.

L. S. Richter and T. R. Gadek, "A Surprising Observation about Mitsunobu Reactions in Solid Phase Synthesis," Tetrahedron Letters, (1994), vol. 35, No. 27, pp. 4705-4706.

\* cited by examiner

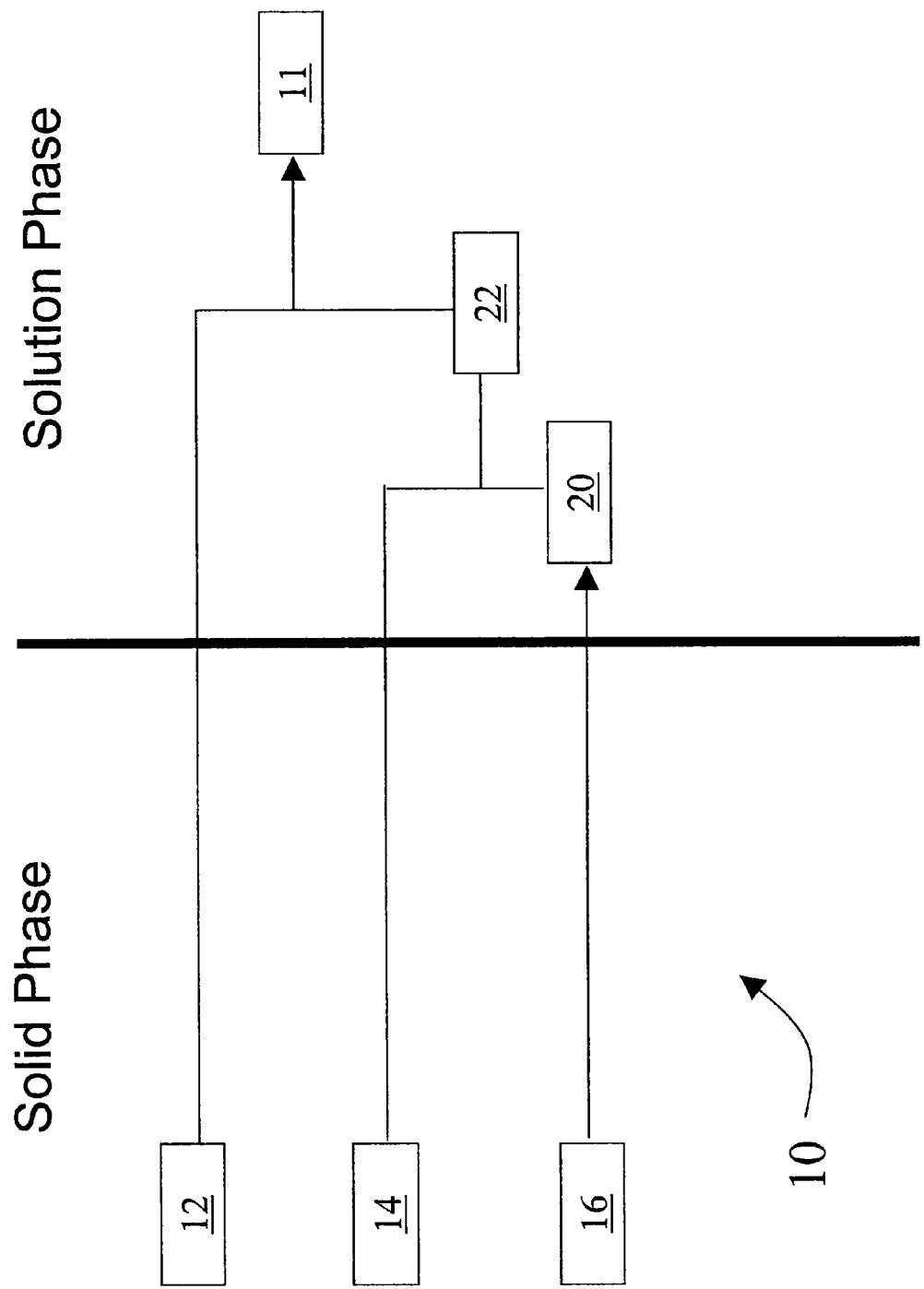

SEQUENCE LISTING

<160> NUMBER OF SEQ ID NOS: 79

<210> SEQ ID NO 1
<211> LENGTH: 39
<212> TYPE: PRT
<213> ORGANISM: Heloderma suspectum

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue

<400> SEQUENCE: 2

His Gly Glu Gly Thr Xaa Xaa Ser Asp Leu Ser Lys Gln Met Glu Glu
1               5                   10                  15

Glu Ala Val

<210> SEQ ID NO 3
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (10)..(11)
<223> OTHER INFORMATION: Forms a psuedoproline residue

<400> SEQUENCE: 3

His Gly Glu Gly Thr Phe Thr Ser Asp Xaa Xaa Lys Gln Met Glu Glu
1               5                   10                  15

Glu Ala Val

<210> SEQ ID NO 4
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 4

His Gly Glu Gly Thr Xaa Xaa Ser Asp Xaa Xaa Lys Gln Met Glu Glu
1               5                   10                  15

-continued

Glu Ala Val

<210> SEQ ID NO 5
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue

<400> SEQUENCE: 5

His Gly Glu Xaa Xaa Phe Thr Ser Asp Leu Ser Lys Gln Met Glu Glu
1               5                   10                  15

Glu Ala Val

<210> SEQ ID NO 6
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 6

His Gly Glu Xaa Xaa Phe Thr Ser Asp Xaa Xaa Lys Gln Met Glu Glu
1               5                   10                  15

Glu Ala Val

<210> SEQ ID NO 7
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue

<400> SEQUENCE: 7

His Gly Glu Xaa Xaa Phe Xaa Xaa Asp Leu Ser Lys Gln Met Glu Glu
1               5                   10                  15

Glu Ala Val

<210> SEQ ID NO 8
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE

```
<222> LOCATION: (6)..(7)
<223> OTHER INFORMATION: Forms a psuedoproline residue

<400> SEQUENCE: 8

His Gly Glu Xaa Xaa Xaa Xaa Ser Asp Leu Ser Lys Gln Met Glu Glu
1               5                   10                  15

Glu Ala Val

<210> SEQ ID NO 9
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue

<400> SEQUENCE: 9

His Gly Glu Gly Thr Phe Xaa Xaa Asp Leu Ser Lys Gln Met Glu Glu
1               5                   10                  15

Glu Ala Val

<210> SEQ ID NO 10
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 10

His Gly Glu Gly Thr Phe Xaa Xaa Asp Xaa Xaa Lys Gln Met Glu Glu
1               5                   10                  15

Glu Ala Val

<210> SEQ ID NO 11
<211> LENGTH: 19
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 11

His Gly Glu Xaa Xaa Phe Xaa Xaa Asp Xaa Xaa Lys Gln Met Glu Glu
1               5                   10                  15

Glu Ala Val
```

-continued

```
<210> SEQ ID NO 12
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue

<400> SEQUENCE: 12

His Gly Glu Gly Thr Xaa Xaa Ser Asp Leu Ser Lys Gln Met Glu Glu
1               5                   10                  15

Glu Ala

<210> SEQ ID NO 13
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (10)..(11)
<223> OTHER INFORMATION: Forms a psuedoproline residue

<400> SEQUENCE: 13

His Gly Glu Gly Thr Phe Thr Ser Asp Xaa Xaa Lys Gln Met Glu Glu
1               5                   10                  15

Glu Ala

<210> SEQ ID NO 14
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 14

His Gly Glu Gly Thr Xaa Xaa Ser Asp Xaa Xaa Lys Gln Met Glu Glu
1               5                   10                  15

Glu Ala

<210> SEQ ID NO 15
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue

<400> SEQUENCE: 15

His Gly Glu Xaa Xaa Phe Thr Ser Asp Leu Ser Lys Gln Met Glu Glu
1               5                   10                  15

Glu Ala
```

```
<210> SEQ ID NO 16
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 16

His Gly Glu Xaa Xaa Phe Thr Ser Asp Xaa Xaa Lys Gln Met Glu Glu
1               5                   10                  15

Glu Ala

<210> SEQ ID NO 17
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue

<400> SEQUENCE: 17

His Gly Glu Xaa Xaa Phe Xaa Xaa Asp Leu Ser Lys Gln Met Glu Glu
1               5                   10                  15

Glu Ala

<210> SEQ ID NO 18
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (6)..(7)
<223> OTHER INFORMATION: Forms a psuedoproline residue

<400> SEQUENCE: 18

His Gly Glu Xaa Xaa Xaa Xaa Ser Asp Leu Ser Lys Gln Met Glu Glu
1               5                   10                  15

Glu Ala

<210> SEQ ID NO 19
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
```

<400> SEQUENCE: 19

His Gly Glu Gly Thr Phe Xaa Xaa Asp Leu Ser Lys Gln Met Glu Glu
1               5                   10                  15

Glu Ala

<210> SEQ ID NO 20
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 20

His Gly Glu Gly Thr Phe Xaa Xaa Asp Xaa Xaa Lys Gln Met Glu Glu
1               5                   10                  15

Glu Ala

<210> SEQ ID NO 21
<211> LENGTH: 18
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 21

His Gly Glu Xaa Xaa Phe Xaa Xaa Asp Xaa Xaa Lys Gln Met Glu Glu
1               5                   10                  15

Glu Ala

<210> SEQ ID NO 22
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue

<400> SEQUENCE: 22

His Gly Glu Gly Thr Xaa Xaa Ser Asp Leu Ser Lys Gln Met Glu Glu
1               5                   10                  15

Glu

<210> SEQ ID NO 23
<211> LENGTH: 17
<212> TYPE: PRT

```
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (10)..(11)
<223> OTHER INFORMATION: Forms a psuedoproline residue

<400> SEQUENCE: 23

His Gly Glu Gly Thr Phe Thr Ser Asp Xaa Xaa Lys Gln Met Glu Glu
1               5                   10                  15

Glu

<210> SEQ ID NO 24
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 24

His Gly Glu Gly Thr Xaa Xaa Ser Asp Xaa Xaa Lys Gln Met Glu Glu
1               5                   10                  15

Glu

<210> SEQ ID NO 25
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue

<400> SEQUENCE: 25

His Gly Glu Xaa Xaa Phe Thr Ser Asp Leu Ser Lys Gln Met Glu Glu
1               5                   10                  15

Glu

<210> SEQ ID NO 26
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 26

His Gly Glu Xaa Xaa Phe Thr Ser Asp Xaa Xaa Lys Gln Met Glu Glu
1               5                   10                  15

Glu
```

```
<210> SEQ ID NO 27
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue

<400> SEQUENCE: 27

His Gly Glu Xaa Xaa Phe Xaa Xaa Asp Leu Ser Lys Gln Met Glu Glu
1               5                   10                  15

Glu

<210> SEQ ID NO 28
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (6)..(7)
<223> OTHER INFORMATION: Forms a psuedoproline residue

<400> SEQUENCE: 28

His Gly Glu Xaa Xaa Xaa Xaa Ser Asp Leu Ser Lys Gln Met Glu Glu
1               5                   10                  15

Glu

<210> SEQ ID NO 29
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue

<400> SEQUENCE: 29

His Gly Glu Gly Thr Phe Xaa Xaa Asp Leu Ser Lys Gln Met Glu Glu
1               5                   10                  15

Glu

<210> SEQ ID NO 30
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue
```

```
<400> SEQUENCE: 30

His Gly Glu Gly Thr Phe Xaa Xaa Asp Xaa Xaa Lys Gln Met Glu Glu
1               5                   10                  15

Glu

<210> SEQ ID NO 31
<211> LENGTH: 17
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 31

His Gly Glu Xaa Xaa Phe Xaa Xaa Asp Xaa Xaa Lys Gln Met Glu Glu
1               5                   10                  15

Glu

<210> SEQ ID NO 32
<211> LENGTH: 19
<212> TYPE: PRT
<213> ORGANISM: Artificial
<220> FEATURE:
<223> OTHER INFORMATION: Chemically synthesized peptide

<400> SEQUENCE: 32

His Gly Glu Gly Thr Phe Thr Ser Asp Leu Ser Lys Gln Met Glu Glu
1               5                   10                  15

Glu Ala Val

<210> SEQ ID NO 33
<211> LENGTH: 18
<212> TYPE: PRT
<213> ORGANISM: Artificial
<220> FEATURE:
<223> OTHER INFORMATION: Chemically synthesized peptide

<400> SEQUENCE: 33

His Gly Glu Gly Thr Phe Thr Ser Asp Leu Ser Lys Gln Met Glu Glu
1               5                   10                  15

Glu Ala

<210> SEQ ID NO 34
<211> LENGTH: 17
<212> TYPE: PRT
<213> ORGANISM: Artificial
<220> FEATURE:
<223> OTHER INFORMATION: Chemically synthesized peptide

<400> SEQUENCE: 34

His Gly Glu Gly Thr Phe Thr Ser Asp Leu Ser Lys Gln Met Glu Glu
1               5                   10                  15

Glu
```

```
<210> SEQ ID NO 35
<211> LENGTH: 9
<212> TYPE: PRT
<213> ORGANISM: Artificial
<220> FEATURE:
<223> OTHER INFORMATION: Chemically synthesized peptide

<400> SEQUENCE: 35

Ala Val Arg Leu Phe Ile Glu Trp Leu
1               5

<210> SEQ ID NO 36
<211> LENGTH: 13
<212> TYPE: PRT
<213> ORGANISM: Artificial
<220> FEATURE:
<223> OTHER INFORMATION: Chemically synthesized peptide

<400> SEQUENCE: 36

Ala Val Arg Leu Phe Ile Glu Trp Leu Lys Asn Gly Gly
1               5                   10

<210> SEQ ID NO 37
<211> LENGTH: 10
<212> TYPE: PRT
<213> ORGANISM: Artificial
<220> FEATURE:
<223> OTHER INFORMATION: Chemically synthesized peptide

<400> SEQUENCE: 37

Arg Leu Phe Ile Glu Trp Leu Lys Asn Gly
1               5                   10

<210> SEQ ID NO 38
<211> LENGTH: 8
<212> TYPE: PRT
<213> ORGANISM: Artificial
<220> FEATURE:
<223> OTHER INFORMATION: Chemically synthesized peptide

<400> SEQUENCE: 38

Val Arg Leu Phe Ile Glu Trp Leu
1               5

<210> SEQ ID NO 39
<211> LENGTH: 11
<212> TYPE: PRT
<213> ORGANISM: Artificial
<220> FEATURE:
<223> OTHER INFORMATION: Chemically synthesized peptide

<400> SEQUENCE: 39

Val Arg Leu Phe Ile Glu Trp Leu Lys Asn Gly
1               5                   10

<210> SEQ ID NO 40
<211> LENGTH: 13
<212> TYPE: PRT
<213> ORGANISM: Artificial
<220> FEATURE:
<223> OTHER INFORMATION: Chemically synthesized peptide

<400> SEQUENCE: 40

Leu Lys Asn Gly Gly Pro Ser Ser Gly Ala Pro Pro Pro
1               5                   10

<210> SEQ ID NO 41
```

```
<211> LENGTH: 12
<212> TYPE: PRT
<213> ORGANISM: Artificial
<220> FEATURE:
<223> OTHER INFORMATION: Chemically synthesized peptide

<400> SEQUENCE: 41

Lys Asn Gly Gly Pro Ser Ser Gly Ala Pro Pro Pro
1               5                   10

<210> SEQ ID NO 42
<211> LENGTH: 9
<212> TYPE: PRT
<213> ORGANISM: Artificial
<220> FEATURE:
<223> OTHER INFORMATION: Chemically synthesized peptide

<400> SEQUENCE: 42

Gly Pro Ser Ser Gly Ala Pro Pro Pro
1               5

<210> SEQ ID NO 43
<211> LENGTH: 14
<212> TYPE: PRT
<213> ORGANISM: Artificial
<220> FEATURE:
<223> OTHER INFORMATION: Chemically synthesized peptide

<400> SEQUENCE: 43

Leu Lys Asn Gly Gly Pro Ser Ser Gly Ala Pro Pro Pro Ser
1               5                   10

<210> SEQ ID NO 44
<211> LENGTH: 13
<212> TYPE: PRT
<213> ORGANISM: Artificial
<220> FEATURE:
<223> OTHER INFORMATION: Chemically synthesized peptide

<400> SEQUENCE: 44

Lys Asn Gly Gly Pro Ser Ser Gly Ala Pro Pro Pro Ser
1               5                   10

<210> SEQ ID NO 45
<211> LENGTH: 10
<212> TYPE: PRT
<213> ORGANISM: Artificial
<220> FEATURE:
<223> OTHER INFORMATION: Chemically synthesized peptide

<400> SEQUENCE: 45

Gly Pro Ser Ser Gly Ala Pro Pro Pro Ser
1               5                   10

<210> SEQ ID NO 46
<211> LENGTH: 22
<212> TYPE: PRT
<213> ORGANISM: Artificial
<220> FEATURE:
<223> OTHER INFORMATION: Chemically synthesized peptide

<400> SEQUENCE: 46

Ala Val Arg Leu Phe Ile Glu Trp Leu Lys Asn Gly Gly Pro Ser Ser
1               5                   10                  15

Gly Ala Pro Pro Pro Ser
            20
```

```
<210> SEQ ID NO 47
<211> LENGTH: 20
<212> TYPE: PRT
<213> ORGANISM: Artificial
<220> FEATURE:
<223> OTHER INFORMATION: Chemically synthesized peptide

<400> SEQUENCE: 47

Arg Leu Phe Ile Glu Trp Leu Lys Asn Gly Gly Pro Ser Ser Gly Ala
1               5                   10                  15

Pro Pro Pro Ser
            20

<210> SEQ ID NO 48
<211> LENGTH: 21
<212> TYPE: PRT
<213> ORGANISM: Artificial
<220> FEATURE:
<223> OTHER INFORMATION: Chemically synthesized peptide

<400> SEQUENCE: 48

Val Arg Leu Phe Ile Glu Trp Leu Lys Asn Gly Gly Pro Ser Ser Gly
1               5                   10                  15

Ala Pro Pro Pro Ser
            20

<210> SEQ ID NO 49
<211> LENGTH: 20
<212> TYPE: PRT
<213> ORGANISM: Artificial
<220> FEATURE:
<223> OTHER INFORMATION: Chemically synthesized peptide

<400> SEQUENCE: 49

Val Arg Leu Phe Ile Glu Trp Leu Lys Asn Gly Pro Ser Ser Gly Ala
1               5                   10                  15

Pro Pro Pro Ser
            20

<210> SEQ ID NO 50
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue

<400> SEQUENCE: 50

His Gly Glu Gly Thr Xaa Xaa Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 51
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (10)..(11)
```

```
<223> OTHER INFORMATION: Forms a psuedoproline residue

<400> SEQUENCE: 51

His Gly Glu Gly Thr Phe Thr Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 52
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 52

His Gly Glu Gly Thr Xaa Xaa Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 53
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue

<400> SEQUENCE: 53

His Gly Glu Xaa Xaa Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 54
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 54
```

-continued

```
His Gly Glu Xaa Xaa Phe Thr Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 55
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue

<400> SEQUENCE: 55

His Gly Glu Xaa Xaa Phe Xaa Xaa Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 56
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (6)..(7)
<223> OTHER INFORMATION: Forms a psuedoproline residue

<400> SEQUENCE: 56

His Gly Glu Xaa Xaa Xaa Xaa Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 57
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue

<400> SEQUENCE: 57

His Gly Glu Gly Thr Phe Xaa Xaa Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 58
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 58

His Gly Glu Gly Thr Phe Xaa Xaa Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 59
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 59

His Gly Glu Xaa Xaa Phe Xaa Xaa Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 60
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue

<400> SEQUENCE: 60

His Gly Glu Gly Thr Xaa Xaa Ser Asp Leu Ser Lys Gln Met Glu Glu
```

```
1               5                   10                  15
Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 61
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (10)..(11)
<223> OTHER INFORMATION: Forms a psuedoproline residue

<400> SEQUENCE: 61

His Gly Glu Gly Thr Phe Thr Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 62
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 62

His Gly Glu Gly Thr Xaa Xaa Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35

<210> SEQ ID NO 63
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue

<400> SEQUENCE: 63

His Gly Glu Xaa Xaa Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

```
<210> SEQ ID NO 64
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 64

His Gly Glu Xaa Xaa Phe Thr Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 65
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue

<400> SEQUENCE: 65

His Gly Glu Xaa Xaa Phe Xaa Xaa Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 66
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (6)..(7)
<223> OTHER INFORMATION: Forms a psuedoproline residue

<400> SEQUENCE: 66

His Gly Glu Xaa Xaa Xaa Xaa Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
```

<210> SEQ ID NO 67
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue

<400> SEQUENCE: 67

His Gly Glu Gly Thr Phe Xaa Xaa Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 68
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 68

His Gly Glu Gly Thr Phe Xaa Xaa Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 69
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 69

His Gly Glu Xaa Xaa Phe Xaa Xaa Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 70
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue

<400> SEQUENCE: 70

His Gly Glu Gly Thr Xaa Xaa Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 71
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (10)..(11)
<223> OTHER INFORMATION: Forms a psuedoproline residue

<400> SEQUENCE: 71

His Gly Glu Gly Thr Phe Thr Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 72
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (6)..(7)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 72

His Gly Glu Gly Thr Xaa Xaa Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 73
<211> LENGTH: 39
<212> TYPE: PRT

```
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue

<400> SEQUENCE: 73

His Gly Glu Xaa Xaa Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 74
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 74

His Gly Glu Xaa Xaa Phe Thr Ser Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 75
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue

<400> SEQUENCE: 75

His Gly Glu Xaa Xaa Phe Xaa Xaa Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 76
<211> LENGTH: 39
<212> TYPE: PRT
<213> ORGANISM: Artificial
<220> FEATURE:
<223> OTHER INFORMATION: Chemically synthesized peptide
```

```
<220> FEATURE:
<221> NAME/KEY: MISC_FEATURE
<222> LOCATION: (4)..(5)
<223> OTHER INFORMATION: Forms a psuedoproline residue
<220> FEATURE:
<221> NAME/KEY: MISC_FEATURE
<222> LOCATION: (6)..(7)
<223> OTHER INFORMATION: Forms a psuedoproline residue

<400> SEQUENCE: 76

His Gly Glu Xaa Xaa Xaa Xaa Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 77
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue

<400> SEQUENCE: 77

His Gly Glu Gly Thr Phe Xaa Xaa Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 78
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 78

His Gly Glu Gly Thr Phe Xaa Xaa Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 79
<211> LENGTH: 39
<212> TYPE: PRT
<213> ORGANISM: Artificial
<220> FEATURE:
<223> OTHER INFORMATION: Chemically synthesized peptide
<220> FEATURE:
<221> NAME/KEY: MISC_FEATURE
<222> LOCATION: (4)..(5)
```

```
<223> OTHER INFORMATION: Forms a psuedoproline residue
<220> FEATURE:
<221> NAME/KEY: MISC_FEATURE
<222> LOCATION: (7)..(8)
<223> OTHER INFORMATION: Forms a psuedoproline residue
<220> FEATURE:
<221> NAME/KEY: MISC_FEATURE
<222> LOCATION: (10)..(11)
<223> OTHER INFORMATION: Forms a psuedoproline residue

<400> SEQUENCE: 79

His Gly Glu Xaa Xaa Phe Xaa Xaa Asp Xaa Xaa Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

INSULINOTROPIC PEPTIDE SYNTHESIS USING SOLID AND SOLUTION PHASE COMBINATION TECHNIQUES

PRIORITY CLAIM

The present non-provisional patent application claims benefit from U.S. Provisional Patent Application having Ser. No. 61/000,622, filed on Oct. 27, 2007, by King, et al., and titled INSULINOTROPIC PEPTIDE SYNTHESIS USING SOLID AND SOLUTION PHASE COMBINATION TECHNIQUES, wherein the entirety of said provisional patent application is incorporated herein by reference.

FIELD OF THE INVENTION

The invention relates to methods for preparing insulinotropic peptides, particularly Exenatide and counterparts thereof, using solid- and solution-phase processes. The present invention further relates to intermediate peptide fragments that can be used in these methods.

BACKGROUND OF THE INVENTION

Many methods for peptide synthesis are described in the literature (for example, see U.S. Pat. No. 6,015,881; Mergler et al. (1988) Tetrahedron Letters 29:4005-4008; Mergler et al. (1988) Tetrahedron Letters 29:4009-4012; Kamber et al. (eds), Peptides, Chemistry and Biology, ESCOM, Leiden (1992) 525-526; Riniker et al. (1993) Tetrahedron Letters 49:9307-9320; Lloyd-Williams et al. (1993) Tetrahedron Letters 49:11065-11133; and Andersson et al. (2000) Biopolymers 55:227-250. The various methods of synthesis are distinguished by the physical state of the phase in which the synthesis takes place, namely liquid phase or solid phase.

In solid phase peptide synthesis (SPPS), an amino acid or peptide group is bound to a solid support resin. Then, successive amino acids or peptide groups are attached to the support-bound peptide until the peptide material of interest is formed. The support-bound peptide is then typically cleaved from the support and subject to further processing and/or purification. In some cases, solid phase synthesis yields a mature peptide product; in other cases the peptide cleaved from the support (i.e., a "peptide intermediate fragment") is used in the preparation of a larger, mature peptide product.

Peptide intermediate fragments generated from solid phase processes can be coupled together in the solid phase or in a liquid phase synthetic process (herein referred to as "solution phase synthesis"). Solution phase synthesis can be particularly useful in cases where the synthesis of a useful mature peptide by solid phase is either impossible or not practical. For example, in solid phase synthesis, longer peptides eventually may adopt an irregular conformation while still attached to the solid support, making it difficult to add additional amino acids or peptide material to the growing chain. As the peptide chain becomes longer on the support resin, the efficiency of process steps such as coupling and deprotection may be compromised. This, in turn, can result in longer processing times to compensate for these problems, in addition to incremental losses in starting materials, such as activatable amino acids, co-reagents, and solvents. These problems can increase as the length of the peptide increases.

Therefore, it is relatively uncommon to find mature peptides of greater than 30 amino acids in length synthesized in a single fragment using only a solid phase procedure. Instead, individual fragments may be separately synthesized on the solid phase, and then coupled in the solid and/or solution phase to build the desired peptide product. This approach requires careful selection of fragment candidates. While some general principles can guide fragment selection, quite often empirical testing of fragment candidates is required. Fragment strategies that work in one context may not work in others. Even when reasonable fragment candidates are uncovered, process innovations may still be needed for a synthesis strategy to work under commercially reasonable conditions. Therefore, peptide synthesis using hybrid schemes are often challenging, and in many cases it is difficult to predict what problems are inherent in a synthesis scheme until the actual synthesis is performed.

In solution phase coupling, two peptide intermediate fragments, or a peptide intermediate fragment (or "fragment") and a reactive amino acid, are coupled in an appropriate solvent, usually in the presence of additional reagents that promote the efficiency and quality of the coupling reaction. The peptide intermediate fragments (or "fragment") are reactively arranged so the N-terminal of one fragment becomes coupled to the C-terminal of the other fragment, or vice versa. In addition, side chain protecting groups, which are present during solid phase synthesis, are commonly retained on the fragments during solution phase coupling to ensure the specific reactivity of the terminal ends of the fragments. These side chain-protecting groups are typically not removed until a mature peptide has been formed.

Modest improvements in one or more steps in the overall synthetic scheme can amount to significant improvements in the preparation of the mature peptide. Such improvements can lead to a large overall saving in time and reagents, and can also significantly improve the purity and yield of the final product. Proper selection of chemical strategies is necessary for this hybrid approach as there are significant pitfalls due to poor solubility of fully protected fragments and due to the ease of epimerization in solution phase couplings.

While the discussion of the importance of improvements in hybrid synthesis is applicable to any sort of peptide produced using these procedures, it is of particular importance in the context of peptides that are therapeutically useful and that are manufactured on a scale for commercial medical use. Synthesis of larger biomolecular pharmaceuticals, such as therapeutic peptides, can be very expensive. Because of the cost of reagents, synthesis time, many synthesis steps, in addition to other factors, very small improvements in the synthetic process of these larger biomolecular pharmaceuticals can have a significant impact on whether it is even economically feasible to produce such a pharmaceutical. Such improvements are necessary due to these high production costs for larger biomolecular pharmaceuticals as supported by the fact that, in many cases, there are few, if any, suitable therapeutic alternatives for these types of larger biomolecular pharmaceuticals.

This is clearly seen in the case of insulinotropic peptides such as the Exenatide peptide and its functional counterparts. Such peptides are possible therapeutic agents for the treatment of type 2 non-insulin-dependent diabetes mellitus and obesity. The peptides improve the initial rapid release of endogenous insulin, suppress glucagon release of the pancreas, regulate gastric emptying, and reduce appetite—all of which function to lower blood glucose. Exenatide is self-regulating in that it lowers blood sugar when levels are elevated but does not continue to lower blood sugar when levels return to normal.

Native Exenatide is isolated from the Gila monster and is 39 amino acid residues long. Exenatide has a molecular weight of 4186.6 Daltons. Native Exenatide, referred to as exendin-4 when it is created synthetically, is commercially available under the trade designation BYETTA™ and may be represented by the notation Exenatide(1-39). This notation indicates that the peptide has all amino acids from 1 (N-terminus) through 39 (C-terminus). Exenatide has the amino acid sequence according to SEQ ID NO. 1:

His$^1$-Gly$^2$-Glu$^3$-Gly$^4$-Thr$^5$-Phe$^6$-Thr$^7$-Ser$^8$-Asp$^9$-

Leu$^{10}$-Ser$^{11}$-Lys$^{12}$-Gln$^{13}$-Met$^{14}$-Glu$^{15}$-Glu$^{16}$-Glu$^{17}$-

Ala$^{18}$-Val$^{19}$-Arg$^{20}$-Leu$^{21}$-Phe$^{22}$-Ile$^{23}$-Glu$^{24}$-Trp$^{25}$-

Leu$^{26}$-Lys$^{27}$-Asn$^{28}$-Gly$^{29}$-Gly$^{30}$-Pro$^{31}$-Ser$^{32}$-Ser$^{33}$-

Gly$^{34}$-Ala$^{35}$-Pro$^{36}$-Pro$^{37}$-Pro$^{38}$-Ser$^{39}$

A key challenge in the solid and solution phase synthesis of Exenatide relates to the sequence of three glutamic acid residues in the 15, 16 and 17 positions. Indeed, any peptide having at least two glutamic acid residues in sequence like this will tend to share this challenge. Specifically, it is difficult to chemically synthesize peptide fragments very far beyond such glutamic acid residues. Without wishing to be bound by theory, the repeating Glu sequence tends to yield a fragment portion that twists in the solid phase. This makes it relatively difficult to continue to build fragment size through the Glu chain effectively. In conventional practice, a fragment having a sequence of two or more repeating Glu residues might only be able to have 1 to 3 amino acids upstream (toward the C terminus) and/or downstream (toward the N-terminus) as a practical matter. The issue tends to be more severe downstream from the repeating Glu chain. This often may mean that peptide fragments grown in the solid phase that contain a sequence of repeating Glu residues tend to be relatively short.

In the case of Exenatide, this has impacted solid phase fragment strategy. In one instance, a fragment scission point might be positioned within the Glu sequence so that one fragment includes only one Glu residue. This strategy in the context of the Exenatide peptide, though, still leaves the other fragment with two Glu residues in a row and may dictate a four fragment synthesis strategy in the solid phase before fragments are coupled in the solution phase. Alternatively, all three Glu residues can be included in one fragment. However, using conventional strategies, this may mean that after the third Glu residue is added to the fragment under construction, it might only be practical to add the Met, the Met and Gln, or possibly the Met, Gln and Lys residues to that fragment, leaving the remaining residues to be assembled in a separate peptide fragment. Again, this may dictate a four fragment synthesis strategy in the solid phase before fragments are coupled in the solution phase. While a four fragment synthesis approach may be desirable in some instances, the conventional handling of the repeating Glu sequences makes even these strategies more problematic than would be desired.

In short, practical concerns associated with repeating Glu sequences may cause a synthesis strategy to resort to extra fragments to ensure that the fragments incorporating the repeating Glu residues are relatively short. It would be highly desirable to be able to use solid phase synthesis to synthesize longer fragments that include two or more Glu residues in a row.

In addition to these concerns, issues relating to product recovery and product purity for the large-scale production of peptides, as well as reagent handling, storage and disposal, can greatly impact the feasibility of the peptide synthesis scheme. Thus, there is a continuing need for peptide synthesis processes capable of efficiently producing peptide materials of commercial interest in large batch quantities with improved yields.

SUMMARY OF THE INVENTION

The present invention relates to the preparation of peptides that are synthesized using a solid and solution phase ("hybrid") approach wherein the peptides include two or more adjacent Glu residues in the peptides amino acid sequence. It has been found that long peptide fragments incorporating these repeating Glu sequences can be readily synthesized when the fragments also incorporate one or more pseudoproline(s) residues as a substitute for two corresponding amino acid residues. Without wishing to be bound by theory, it is believed that the one or more pseudoproline(s) help to stiffen the growing fragment, making it much easier to continue to add significantly more amino acids to the growing chain than can be practically accomplished in the absence of the one or more pseudoproline(s). Schematically, the pseudoproline(s) can be viewed as an in situ scaffold that helps hold the growing peptide fragment in a structural conformation more amenable to incorporating additional amino acid residues into the growing peptide chain. During de-protection, the pseudoprolines are easily modified to yield the desired pair of amino acid residues for which the pseudoproline was substituted in the first instance. A pseudoproline can be substituted upstream (toward the C-terminus) to allow more upstream amino acid residues to precede the repeating Glu sequence or downstream (toward the N-terminus) to allow more downstream amino acid residues to be added to the peptide fragments after the Glu residues. Downstream is more preferred, as the benefit is more pronounced.

Generally, it is desirable if the pseudoproline residue is incorporated into a peptide or peptide fragment so that no more than 8, preferably no more than 5 intervening amino acid residues are between the pseudoproline residue and the repeating Glu chain and/or another pseudoproline residue. The benefits of a pseudoproline residue may last for several additional amino acid residues, so it is desirable that at least two or more amino acid residues are positioned between pseudoproline residues in those embodiments where more than one pseudoproline is incorporated into the peptide or peptide fragment.

The principles of the present invention are applicable to insulinotropic peptides such as the Exenatide peptide, which includes a repeating sequence of three Glu residues in the 15, 16, and 17 positions, as well as natural and non-natural counterparts thereof, and intermediate peptide fragments of these. By using at least one pseudoproline, for instance, the Exenatide peptide and counterparts thereof are easily synthesized in only three different peptide intermediate fragments using solid phase chemistry. Solution phase chemistry is then used to add additional amino acid material to one of the fragments. The fragments are then coupled together in solution phase.

The use of a pseudoproline in one of the Exenatide fragments allows the fragment to be quite long even though this fragment may include the sequence of repeating Glu residues, eases the solid phase synthesis of that fragment, and also eases the subsequent solution phase coupling of this fragment to other fragments. Without using at least one pseudoproline, at least four peptide fragments would be needed to apply a hybrid synthesis effectively. For example, the fragments such as Exenatide(1-17), Exenatide(1-19), and Exenatide(1-20) (all of which include a Glu-Glu-Glu sequence) are very readily synthesized using pseudoproline substitution(s) in high yield and purity, whereas only much shorter fragments including the Glu-Glu-Glu sequence can be synthesized in comparable yield and purity in the absence of using pseudoproline substitution(s).

In one aspect, the present invention relates to an insulinotropic peptide fragment, comprising an amino acid sequence comprised of at least two glutamic acid residues in direct sequence (Glu-Glu) and further comprising a residue of at least one pseudoproline moiety, said fragment optionally containing side chain protection.

In another aspect, the present invention relates to a method of making an insulinotropic peptide, comprising the steps of:
a) preparing a first peptide fragment or a counterpart thereof including an amino acid sequence comprising at least two glutamates in direct sequence (Glu-Glu) and further comprising a pseudoproline; and
b) incorporating the peptide fragment into an insulinotropic peptide.

In another aspect, the present invention relates to an insulinotropic peptide, comprising:
at least one residue of a pseudoproline; at least two glutamic acid residues in direct sequence (Glu-Glu); and optionally at least one protecting group.

In another aspect, the present invention relates to a peptide fragment selected from the group consisting of a fragment according to any one of SEQ ID Nos. 35-39 or a counterpart thereof.

In another aspect, the present invention relates to a peptide fragment selected from the group consisting of a fragment according to any one of SEQ ID Nos. 40-42 or a counterpart thereof.

In another aspect, the present invention relates to a peptide fragment selected from the group consisting of a fragment according to any one of SEQ ID Nos. 43-45 or a counterpart thereof.

In another aspect, the present invention relates to a peptide fragment selected from the group consisting of a fragment according to any one of SEQ ID Nos. 46-49 or a counterpart thereof.

In another aspect, the present invention relates to a method of making an insulinotropic peptide, comprising the steps of: a) providing first, second, and third peptide fragments, said first fragment including a sequence of at least two repeating Glu residues and including at least one residue of a pseudoproline, and wherein any of said fragments optionally including at least one protecting group; b) coupling a Serine residue to the third peptide fragment to obtain a fourth peptide fragment; c) coupling the fourth fragment to the second fragment to obtain a fifth fragment; d) coupling the fifth peptide fragment to the first peptide fragment to obtain an insulinotropic peptide.

BRIEF DESCRIPTION OF THE DRAWINGS

FIG. 1 is a schematic diagram of a synthesis scheme in accordance with the present invention.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

All patents, published patent applications, other publications, and pending patent applications cited in this specification are incorporated by reference herein in their respective entireties for all purposes.

The present invention is directed to synthetic methods for making peptides and peptide fragments that include two or more adjacent Glu residues, preferably three or more adjacent Glu residues in the amino acid sequence of the peptide. Peptide molecules of the invention may be protected, unprotected, or partially protected. Protection may include N-terminus protection, side chain protection, and/or C-terminus protection. In preferred embodiments, the invention is generally directed at the synthesis of insulinotropic peptides having such repeating Glu residues and their counterparts, fragments and their counterparts, and fusion products and their counterparts of these. Most preferably, the invention is used to synthesize exendins such as Exenatide, counterparts of Exenatide, and fragments thereof.

As used herein, a "counterpart" refers to natural and non-natural analogs, derivatives, fusion compounds, salts, or the like of a peptide. As used herein, a peptide analog generally refers to a peptide having a modified amino acid sequence such as by one or more amino acid substitutions, deletions, inversions, and/or additions relative to another peptide or peptide counterpart. Substitutions may involve one or more natural or non-natural amino acids. Substitutions preferably may be conservative or highly conservative. A conservative substitution refers to the substitution of an amino acid with another that has generally the same net electronic charge and generally the same size and shape. For instance, amino acids with aliphatic or substituted aliphatic amino acid side chains have approximately the same size when the total number of carbon and heteroatoms in their side chains differs by no more than about four. They have approximately the same shape when the number of branches in the their side chains differs by no more than about one or two. Amino acids with phenyl or substituted phenyl groups in their side chains are considered to have about the same size and shape. Listed below are five groups of amino acids. Replacing an amino acid in a compound with another amino acid from the same groups generally results in a conservative substitution.

Group I: glycine, alanine, valine, leucine, isoleucine, serine, threonine, cysteine, methionine and non-naturally occurring amino acids with $C_1$-$C_4$ aliphatic or $C_1$-$C_4$ hydroxyl substituted aliphatic side chains (straight chained or monobranched).

Group II: glutamic acid, aspartic acid and nonnaturally occurring amino acids with carboxylic acid substituted $C_1$-$C_4$ aliphatic side chains (unbranched or one branch point).

Group III: lysine, ornithine, arginine and nonnaturally occurring amino acids with amine or guanidino substituted $C_1$-$C_4$ aliphatic side chains (unbranched or one branch point).

Group IV: glutamine, asparagine and non-naturally occurring amino acids with amide substituted $C_1$-$C_4$ aliphatic side chains (unbranched or one branch point).

Group V: phenylalanine, phenylglycine, tyrosine and tryptophan.

A "highly conservative substitution" is the replacement of an amino acid with another amino acid that has the same functional group in the side chain and nearly the same size and shape. Amino acids with aliphatic or substituted aliphatic amino acid side chains have nearly the same size when the total number carbon and heteroatoms in their side chains differs by no more than two. They have nearly the same shape when they have the same number of branches in the their side chains. Examples of highly conservative substitutions include valine for leucine, threonine for serine, aspartic acid for glutamic acid and phenylglycine for phenylalanine.

A peptide derivative generally refers to a peptide, a peptide analog, or other peptide counterpart having chemical modification of one or more of its side groups, alpha carbon atoms, terminal amino group, and/or terminal carboxyl acid group. By way of example, a chemical modification includes, but is not limited to, adding chemical moieties, creating new bonds, and/or removing chemical moieties. Modifications at amino acid side groups include, without limitation, acylation of lysine ε-amino groups, N-alkylation of arginine, histidine, or lysine, alkylation of glutamic or aspartic carboxylic acid groups, and deamidation of glutamine or asparagine. Modifications of the terminal amino group include, without limitation, the des-amino, N-lower alkyl, N-di-lower alkyl, and N-acyl (e.g., —CO-lower alkyl) modifications. Modifications of the terminal carboxy group include, without limitation, the amide, lower alkyl amide, dialkyl amide, and lower alkyl ester modifications. Thus, partially or wholly protected peptides constitute peptide derivatives.

In the practice of the present invention, a compound has "insulinotropic" activity if it is able to stimulate, or cause the stimulation of, or help cause the stimulation of the synthesis or expression of the hormone insulin. In preferred modes of practice, insulinotropic activity can be demonstrated according to assays described in U.S. Pat. Nos. 6,887,849 and 6,703,365.

For purposes of illustration, the principles of the present invention will now be described with reference to FIG. 1 in the context of synthesizing the Exenatide peptide 11 having the following formula (SEQ. ID NO. 1):

His$^1$-Gly$^2$-Glu$^3$-Gly$^4$-Thr$^5$-Phe$^6$-Thr$^7$-Ser$^8$-Asp$^9$-

Leu$^{10}$-Ser$^{11}$-Lys$^{12}$-Gln$^{13}$-Met$^{14}$-Glu$^{15}$-Glu$^{16}$-Glu$^{17}$-

Ala$^{18}$-Val$^{19}$-Arg$^{20}$-Leu$^{21}$-Phe$^{22}$-Ile$^{23}$-Glu$^{24}$-Trp$^{25}$-

Leu$^{26}$-Lys$^{27}$-Asn$^{28}$-Gly$^{29}$-Gly$^{30}$-Pro$^{31}$-Ser$^{32}$-Ser$^{33}$-

Gly$^{34}$-Ala$^{35}$-Pro$^{36}$-Pro$^{37}$-Pro$^{38}$-Ser$^{39}$

The scheme 10 of FIG. 1 is believed to be particularly suitable for the scaled-up synthesis of Exenatide peptides and their counterparts. Scaled-up procedures are typically performed to provide an amount of peptide useful for commercial distribution. For example, the amount of peptide in a scaled-up procedure can be 500 g, or 1 kg per batch, and more typically tens of kg to hundreds of kg per batch or more. In preferred embodiments, the inventive methods can provide such improvements as reduction in processing (synthesis) time, improvements in the yield of products, improvements in product purity, and/or reduction in amount of reagents and starting materials required. The synthesis scheme 10 shown in FIG. 1 uses a combination of solid and solution phase techniques to prepare the peptide product 11.

Referring to FIG. 1, scheme 10 involves synthesizing peptide intermediate fragments 12, 14, and 16 on the solid phase. An additional amino acid is coupled to fragment 16 in the solution phase to make fragment 20. Then, the resultant three fragments are assembled in the solution phase to make the full size peptide 11.

Fragment 12 generally includes at least 8 amino acid residues and more desirably extends from His1 through at least one, and preferably at least two, and more preferably at least all three of the Glu residues at positions 15, 16, and 17. One or more pseudoprolines advantageously are incorporated into fragment 12 in order to facilitate synthesis of this relatively large peptide fragment. Until a de-protection step is carried out, the pseudoproline residues used in this fashion will be incorporated into the fragment or larger peptides incorporating the fragment, as the case may be.

As used in the practice of the present invention, the term pseudoproline refers to a dipeptide that includes a residue of a hydroxyl functional amino acid such as Ser or Thr in which the hydroxyl functional side chain is protected as a proline-like, TFA labile, oxazolidine ring between the alpha-amino and the side chain hydroxyl. As a consequence of the oxazolidine ring, the dipeptide functions as a reversible proline mimetic. A pseudoproline generally is substituted into a peptide fragment in place of two adjacent amino acid residues of the target fragment under construction. The portion of the pseudoproline at the C-terminus usually corresponds either to the oxazolidine ring-protected Ser or Thr, while the adjacent portion may correspond to any other amino acid. Accordingly, a typical pseudoproline residue or moiety as incorporated into a peptide may be represented by the general formula

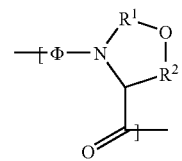

wherein Φ proximal to the N-terminus represents the residue of any amino acid and each of $R^1$ and $R^2$ is independently a suitable divalent linking moiety. Often, $R^1$ is a divalent moiety of the formula

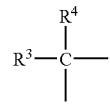

wherein each of $R^3$ and $R^4$ is independently a monovalent moiety such as H, or lower alkyl such as methyl. $R^3$ and $R^4$ also may be co-members of a ring structure. Desirably, each of $R^3$ and $R^4$ independently is methyl or H. In the case of an oxazolidine ring-protected Ser, $R^2$ is the divalent moiety $CH_2$, while in the case of Thr, $R^2$ is the divalent moiety —(CH$_3$)CH—.

During de-protection, the $R^1$ moiety is cleaved to provide a dipeptide residue according to the following formula:

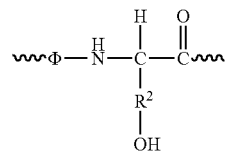

wherein $R^2$ is as defined above.

As applied to fragment 12 of the Exenatide(1-39) peptide 11 shown in FIG. 1, one or more of such pseudoprolines may be substituted into the fragment downstream from the Glu residues at positions 15, 16, and 17 in order to facilitate synthesis of the relatively long fragment. As can be seen from SEQ ID. No. 1, there are Ser or Thr residues at the 5, 7, 8, and 11 positions downstream from the Glu-Glu-Glu residues.

This indicates that one or more pseudoprolines can be substituted into fragment 12 at the Gly-Thr (4-5), Phe-Thr (6-7), Thr-Ser (7-8), and/or Leu-Ser (10-11) positions. Preferably, a pseudoproline is used in at least one of the Phe-Thr (6-7) and/or Leu-Ser (10-11) positions. More preferably, a corresponding pseudoproline is used at each of the Phe-Thr (6-7) and Leu-Ser (10-11) positions. Although a third and fourth pseudoproline could be used if desired, use of the one or two pseudoprolines at these two preferred positions provides adequate performance for relatively easy building of fragment 12 without needing additional pseudoproline contribution.

In a specific illustrative mode of practice, an FMOC-protected pseudoproline suitable for use in place of Leu-Ser at the 10 and 11 positions has the formula

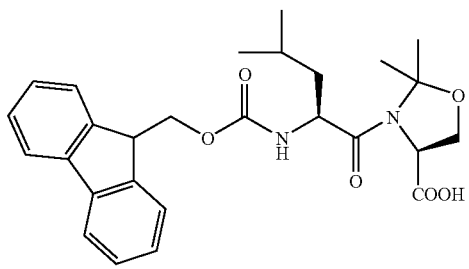 [SMILES: CC(C)C[C@H](NC(=O)OCC1c2ccccc2-c2ccccc21)C(=O)N1[C@H](C(=O)O)COC1(C)C]

wherein the terminal OH indicates the acid functionality available for coupling at the C-terminus. This pseudoproline can be designated by the notation Fmoc-Leu-Ser($\psi^{Me,Me}$-pro)-OH. Similarly, an FMOC-protected pseudoproline suitable for use in place of the Phe-Thr at the 6 and 7 positions has the formula

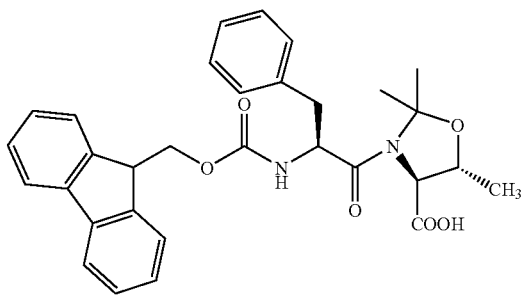 [SMILES: C[C@H]1OC(C)(C)N(C(=O)[C@H](Cc2ccccc2)NC(=O)OCC2c3ccccc3-c3ccccc32)[C@@H]1C(=O)O]

wherein the terminal OH indicates the acid functionality available for coupling at the C-terminus. This pseudoproline can be designated by the notation Fmoc-Phe-Thr($\psi^{Me,Me}$-pro)-OH.

The first fragment 12 desirably has the formula $X^{j,k}$ Exenatide(1–m) fragment wherein j and k are defined as residue positions 4 and 5, 6 and 7, 7 and 8, and/or 10 and 11 with the proviso that a pseudoproline is present at least at one of these positions; each X independently is a pseudoproline moiety; and m is 15 to 20, preferably 17 to 19, more preferably 17 or 19. Thus, it can be appreciated that the first fragment is exceptionally long even though preferred embodiments incorporates a sequence of Glu-Glu-Glu proximal to the C-terminus, where twisting effects can be most problematic for solid phase synthesis.

One or more of the amino acid residues may include side chain protecting groups in accordance with conventional practices. In some embodiments, the peptide Fragment 12 may be resin bound via the C-terminus. This fragment optionally may bear N-terminus and/or C-terminus protection groups. FMOC, Alloc, and Z moieties, respectively, would be a particularly useful N-terminus protecting group with respect to solid phase synthesis of the peptide fragment. FMOC stands for the fluorenyl-methoxy-carbonyl moiety. Alloc refers to the allyloxycarbonyl protecting group. Z refers to the Benzyloxy-carbonyl protecting group.

In representative embodiments, Fragment 12 may include one or more peptide fragments as follows:

```
SEQ ID No.2:
His-Gly-Glu-Gly-Thr-X⁶-X⁷-Ser-Asp-Leu-Ser-Lys-Gln-

Met-Glu-Glu-Glu-Ala-Val

SEQ ID No.3:
His-Gly-Glu-Gly-Thr-Phe-Thr-Ser-Asp-X¹⁰-X¹¹-Lys-

Gln-Met-Glu-Glu-Glu-Ala-Val

SEQ ID No. 4:
His-Gly-Glu-Gly-Thr-X⁶-X⁷-Ser-Asp-X¹⁰-X¹¹-Lys-Gln-

Met-Glu-Glu-Glu-Ala-Val

SEQ ID No. 5:
His-Gly-Glu-X⁴-X⁵-Phe-Thr-Ser-Asp-Leu-Ser-Lys-Gln-

Met-Glu-Glu-Glu-Ala-Val

SEQ ID No. 6:
His-Gly-Glu-X⁴-X⁵-Phe-Thr-Ser-Asp-X¹⁰-X¹¹-Lys-Gln-

Met-Glu-Glu-Glu-Ala-Val

SEQ ID No. 7:
His-Gly-Glu-X⁴-X⁵-Phe-X⁷-X⁸-Asp-Leu-Ser-Lys-Gln-

Met-Glu-Glu-Glu-Ala-Val

SEQ ID No. 8:
His-Gly-Glu-X⁴-X⁵-X⁶-X⁷-Ser-Asp-Leu-Ser-Lys-Gln-

Met-Glu-Glu-Glu-Ala-Val

SEQ ID No. 9:
His-Gly-Glu-Gly-Thr-Phe-X⁷-X⁸-Asp-Leu-Ser-Lys-Gln-

Met-Glu-Glu-Glu-Ala-Val

SEQ ID No. 10:
His-Gly-Glu-Gly-Thr-Phe-X⁷-X⁸-Asp-X¹⁰-X¹¹-Lys-Gln-

Met-Glu-Glu-Glu-Ala-Val

SEQ ID No. 11:
His-Gly-Glu-X⁴-X⁵-Phe-X⁷-X⁸-Asp-X¹⁰-X¹¹-Lys-Gln-

Met-Glu-Glu-Glu-Ala-Val

SEQ ID No. 12:
His-Gly-Glu-Gly-Thr-X⁶-X⁷-Ser-Asp-Leu-Ser-Lys-Gln-

Met-Glu-Glu-Glu-Ala

SEQ ID No. 13:
His-Gly-Glu-Gly-Thr-Phe-Thr-Ser-Asp-X¹⁰-X¹¹-Lys-

Gln-Met-Glu-Glu-Glu-Ala

SEQ ID No. 14:
His-Gly-Glu-Gly-Thr-X⁶-X⁷-Ser-Asp-X¹⁰-X¹¹-Lys-Gln-

Met-Glu-Glu-Glu-Ala

SEQ ID No. 15:
His-Gly-Glu-X⁴-X⁵-Phe-Thr-Ser-Asp-Leu-Ser-Lys-Gln-
```

Met-Glu-Glu-Glu-Ala

SEQ ID No. 16:
His-Gly-Glu-X$^4$-X$^5$-Phe-Thr-Ser-Asp-X$^{10}$-X$^{11}$-Lys-Gln-

Met-Glu-Glu-Glu-Ala

SEQ ID No. 17:
His-Gly-Glu-X$^4$-X$^5$-Phe-X$^7$-X$^8$-Asp-Leu-Ser-Lys-Gln-

Met-Glu-Glu-Glu-Ala

SEQ ID No. 18:
His-Gly-Glu-X$^4$-X$^5$-X$^6$-X$^7$-Ser-Asp-Leu-Ser-Lys-Gln-

Met-Glu-Glu-Glu-Ala

SEQ ID No. 19:
His-Gly-Glu-Gly-Thr-Phe-X$^7$-X$^8$-Asp-Leu-Ser-Lys-Gln-

Met-Glu-Glu-Glu-Ala

SEQ ID No. 20:
His-Gly-Glu-Gly-Thr-Phe-X$^7$-X$^8$-Asp-X$^{10}$-X$^{11}$-Lys-Gln-

Met-Glu-Glu-Glu-Ala

SEQ ID No. 21:
His-Gly-Glu-X$^4$-X$^5$-Phe-X$^7$-X$^8$-Asp-X$^{10}$-X$^{11}$-Lys-Gln-

Met-Glu-Glu-Glu-Ala

SEQ ID No. 22:
His-Gly-Glu-Gly-Thr-X$^6$-X$^7$-Ser-Asp-Leu-Ser-Lys-Gln-

Met-Glu-Glu-Glu

SEQ ID No. 23:
His-Gly-Glu-Gly-Thr-Phe-Thr-Ser-Asp-X$^{10}$-X$^{11}$-Lys-

Gln-Met-Glu-Glu-Glu

SEQ ID No. 24:
His-Gly-Glu-Gly-Thr-X$^6$-X$^7$-Ser-Asp-X$^{10}$-X$^{11}$-Lys-Gln-

Met-Glu-Glu-Glu

SEQ ID No. 25:
His-Gly-Glu-X$^4$-X$^5$-Phe-Thr-Ser-Asp-Leu-Ser-Lys-Gln-

Met-Glu-Glu-Glu

SEQ ID No. 26:
His-Gly-Glu-X$^4$-X$^5$-Phe-Thr-Ser-Asp-X$^{10}$-X$^{11}$-Lys-Gln-

Met-Glu-Glu-Glu

SEQ ID No. 27:
His-Gly-Glu-X$^4$-X$^5$-Phe-X$^7$-X$^8$-Asp-Leu-Ser-Lys-Gln-

Met-Glu-Glu-Glu

SEQ ID No. 28:
His-Gly-Glu-X$^4$-X$^5$-X$^6$-X$^7$-Ser-Asp-Leu-Ser-Lys-Gln-

Met-Glu-Glu-Glu

SEQ ID No. 29:
His-Gly-Glu-Gly-Thr-Phe-X$^7$-X$^8$-Asp-Leu-Ser-Lys-Gln-

Met-Glu-Glu-Glu

SEQ ID No. 30:
His-Gly-Glu-Gly-Thr-Phe-X$^7$-X$^8$-Asp-X$^{10}$-X$^{11}$-Lys-Gln-

Met-Glu-Glu-Glu

SEQ ID No. 31:
His-Gly-Glu-X$^4$-X$^5$-Phe-X$^7$-X$^8$-Asp-X$^{10}$-X$^{11}$-Lys-Gln-

Met-Glu-Glu-Glu wherein in SEQ ID Nos. 2 through 31, the pseudoproline at positions 4 and 5 corresponds to Gly-Thr or a counterpart thereof; the pseudoproline at positions 6 and 7 corresponds to Phe Thr or a counterpart thereof; the pseudoproline at positions 7 and 8 corresponds to Thr-Ser or a counterpart thereof; and the pseudoproline at positions 10 and 11 corresponds to Leu-Ser or a counterpart thereof.

In deprotected form, the pseudoproline-containing fragments according to SEQ ID Nos. 2 through 11 have the amino acid sequence Exenatide(1-19) according to SEQ ID No. 32:

His-Gly-Glu-Gly-Thr-Phe-Thr-Ser-Asp-Leu-Ser-Lys-

Gln-Met-Glu-Glu-Glu-Ala-Val

In deprotected form, the pseudoproline-containing fragments according to SEQ ID Nos. 12 through 21 have the amino acid sequence Exenatide(1-18) according to SEQ ID No. 33:

His-Gly-Glu-Gly-Thr-Phe-Thr-Ser-Asp-Leu-Ser-Lys-

Gln-Met-Glu-Glu-Glu-Ala

In deprotected form, the pseudoproline-containing fragments according to SEQ ID Nos. 22 through 31 have the amino acid sequence Exenatide(1-17) according to SEQ ID No. 34:

His-Gly-Glu-Gly-Thr-Phe-Thr-Ser-Asp-Leu-Ser-Lys-

Gln-Met-Glu-Glu-Glu

Solid phase synthesis is generally carried out in a direction from the C-terminus to the N-terminus of fragment 12. Thus, if Fragment 12 is comprised of 17 amino acid residues, the amino acid in position 17 (Glu-), which is present on the C-terminal portion of the fragment, is the first amino acid residue that is coupled to the solid phase resin support. Solid phase synthesis then proceeds by consecutively adding amino acid residues in a manner corresponding to the desired sequence. The synthesis of the peptide intermediate fragment is complete after the N-terminal residue (for example, the N-terminal histidine residue (His) has been added to the nascent peptide chain.

Fragment 14 is a second peptide fragment that may be generally identified by the notation Exenatide(n-q) wherein n is m+1 (wherein m is defined above with respect to the first fragment as being 15-20) and q is 25 to 30. Thus, the N-terminus of Fragment 14 can be the amino acid residue at any of the 16 to 20 positions, and the C-terminus can be at any of the 25 to 30 positions of Exenatide or a counterpart thereof. In preferred embodiments, n is 18 to 20, and q is 26-30. One or more of the amino acid residues of Fragment 14 may include side chain protecting groups in accordance with conventional practices. In some embodiments, the peptide Fragment 14 may be resin-bound via the C-terminus. This fragment optionally may bear N-terminus and/or C-terminus protection groups. FMOC, Alloc, and Z moieties, respectively, would be a particularly useful N-terminus protecting group with respect to solid phase synthesis of the peptide fragment.

n representative embodiments, Fragment 14 may have an amino acid sequence as follows:

SEQ ID No. 35:
Ala$^{18}$-Val$^{19}$-Arg$^{20}$-Leu$^{21}$-Phe$^{22}$-Ile$^{23}$-Glu$^{24}$-Trp$^{25}$-Leu$^{26}$

SEQ ID No. 36:
Ala$^{18}$-Val$^{19}$-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$

SEQ ID No. 37:
Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$

SEQ ID No. 38:
Val$^{19}$-Arg$^{20}$-Leu$^{21}$-Phe$^{22}$-Ile$^{23}$-Glu$^{24}$-Trp$^{25}$-Leu$^{26}$

SEQ ID No. 39:
Val$^{19}$-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$

As stated previously, solid phase synthesis is generally carried out in a direction from the C-terminus to the N-terminus of the Fragment 14. Thus, if Fragment 14 ends at position 26, the Leucine (Leu) amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. The synthesis of the peptide intermediate fragment is complete after the N-terminal residue (for example, in the case of Fragment 14 ending at position 18, the N-terminal Alanine residue (Ala)) has been added to the nascent peptide chain.

Fragment 16 is a third peptide fragment that may be generally identified by the notation Exenatide(q+1–38) wherein q is defined above with respect to the second fragment. Note that Fragment 16 often does not yet include the Serine (Ser) residue in the 39 residue position at the C terminus of native Exenatide. The Serine often is subsequently coupled to the C terminus of Fragment 16 in the solution phase, preferably using Serine with a side chain protection.

One or more of the amino acid residues of Fragment 16 may include side chain protecting groups in accordance with conventional practices. In some embodiments, the peptide Fragment 16 may be resin-bound via the C-terminus. This fragment optionally may bear N-terminus and/or C-terminus protection groups. FMOC, Alloc, and Z Moieties, respectively, would be a particularly useful N-terminus protecting group with respect to solid phase synthesis of the peptide fragment. In representative embodiments, Fragment 16 may have an amino acid sequence as follows:

SEQ ID No. 40:
Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$

SEQ ID No. 41:
Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$

SEQ ID No. 42:
Gly$^{30}$-Pro$^{31}$-Ser$^{32}$-Ser$^{33}$-Gly$^{34}$-Ala$^{35}$-Pro$^{36}$-Pro$^{37}$-Pro$^{38}$

Solid phase synthesis is generally carried out in a direction from the C-terminus to the N-terminus of Fragment 16. Thus, the Pro$^{38}$ amino acid, which is present on the C-terminal portion of the fragment, is the first amino acid residue that is coupled to the solid phase resin support. Solid phase synthesis then proceeds by consecutively adding amino acid residues in a manner corresponding to the desired sequence. The synthesis of the peptide intermediate fragment is complete after the N-terminal residue (for example, in the embodiment where Fragment 16 comprises Exenatide(27-38), the N-terminal Lysine residue (Lys$^{27}$) has been added to the nascent peptide chain. Any of the amino acids used in the synthesis of Fragment 16 may include side chain protection in accordance with conventional practices.

Continuing to refer to FIG. 1, Fragments 12, 14, and 16, along with Serine, are assembled to complete the desired peptide 11 desirably using solution phase coupling techniques. To the extent that the fragments bear side-chain protecting groups and incorporate pseudoproline residues, these protections are kept in place during solution phase coupling. The N-terminus and C-terminus of the reactants are protected as appropriate as well. To accomplish these couplings, Serine is added to fragment 16 in the solution phase to produce intermediate Fragment 20. By way of example, adding Ser$^{39}$ to various embodiments of fragment 16 may produce one or more fragments 20 such as the following:

SEQ ID No. 43:
Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 44:
Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 45:
Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

Peptide fragments 14 and 20 are then coupled in the solution phase to yield the intermediate protected Fragment 22. By way of example, the following are preferred embodiments of preferred Fragments 22:

SEQ ID No. 46:
Ala$^{18}$-Val$^{19}$-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$Ser$^{39}$

SEQ ID No. 47:
Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$Ser$^{39}$

SEQ ID No. 48:
Val$^{19}$-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$Ser$^{39}$

SEQ ID No. 49:
Val$^{19}$-Arg$^{20}$-Leu$^{21}$-Phe$^{22}$-Ile$^{23}$-Glu$^{24}$-Trp$^{25}$-Lys$^{27}$-Asn$^{28}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$Ser$^{39}$

Peptide Fragments 12 and 22 are then coupled in the solution phase to yield the pseudoproline-containing peptide 11. To the extent that the other amino residues bear side chain protection, this protection desirably is maintained through this step. By way of example, the following are preferred embodiments of the resultant, preferred peptide 11:

SEQ ID No. 50:
His-Gly-Glu-Gly-Thr-X$^6$-X$^7$-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 51:
His-Gly-Glu-Gly-Thr-Phe-Thr-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 52:
His-Gly-Glu-Gly-Thr-X$^6$-X$^7$-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 53:
His-Gly-Glu-X$^4$-X$^5$-Phe-Thr-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 54:
His-Gly-Glu-X$^4$-X$^5$-Phe-Thr-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 55:
His-Gly-Glu-X$^4$-X$^5$-Phe-X$^7$-X$^8$-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 56:
His-Gly-Glu-X$^4$-X$^5$-X$^6$-X$^7$-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 57:
His-Gly-Glu-Gly-Thr-Phe-X$^7$-X$^8$-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 58:
His-Gly-Glu-Gly-Thr-Phe-X$^7$-X$^8$-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser39

SEQ ID No. 59:
His-Gly-Glu-X$^4$-X$^5$-Phe-X$^7$-X$^8$-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser39

SEQ ID No. 60:
His-Gly-Glu-Gly-Thr-X$^6$-X$^7$-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 61:
His-Gly-Glu-Gly-Thr-Phe-Thr-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 62:
His-Gly-Glu-Gly-Thr-X$^6$-X$^7$-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 63:
His-Gly-Glu-X$^4$-X$^5$-Phe-Thr-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 64:
His-Gly-Glu-X$^4$-X$^5$-Phe-Thr-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 65:
His-Gly-Glu-X$^4$-X$^5$-Phe-X$^7$-X$^8$-Asp-Leu-Ser-Lys-Gln-Met-Glu-Glu-Glu-Ala-Val-Arg$^{20}$-Leu$^{21}$-Phe$^{22}$-Ile$^{23}$-

-continued

SEQ ID No. 65:
Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 66:
His-Gly-Glu-X$^4$-X$^5$-X$^6$-X$^7$-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 67:
His-Gly-Glu-Gly-Thr-Phe-X$^7$-X$^8$-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 68:
His-Gly-Glu-Gly-Thr-Phe-X$^7$-X$^8$-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 69:
His-Gly-Glu-X$^4$-X$^5$-Phe-X$^7$-X$^8$-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 70:
His-Gly-Glu-Gly-Thr-X$^6$-X$^7$-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 71:
His-Gly-Glu-Gly-Thr-Phe-Thr-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 72:
His-Gly-Glu-Gly-Thr-X$^6$-X$^7$-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 73:
His-Gly-Glu-X$^4$-X$^5$-Phe-Thr-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 74:
His-Gly-Glu-X$^4$-X$^5$-Phe-Thr-Ser-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 75:
His-Gly-Glu-X$^4$-X$^5$-Phe-X$^7$-X$^8$-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 76:
His-Gly-Glu-X$^4$-X$^5$-X$^6$-X$^7$-Ser-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 77:
His-Gly-Glu-Gly-Thr-Phe-X$^7$-X$^8$-Asp-Leu-Ser-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 78:
His-Gly-Glu-Gly-Thr-Phe-X$^7$-X$^8$-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

SEQ ID No. 79:
His-Gly-Glu-X$^4$-X$^5$-Phe-X$^7$-X$^8$-Asp-X$^{10}$-X$^{11}$-Lys-Gln-Met-Glu-Glu-Glu-Ala-Val-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$

In SEQ ID Nos. 50 through 79, the $X^4$-$X^5$, $X^6$-$X^7$, $X^7$-$X^8$, and $X^{10}$-$X^{11}$ pairs constitute pseudoproline residues, respectively, as defined above.

In carrying out the reaction scheme of FIG. 1, solid phase and solution phase syntheses may be carried out by standard methods known in the industry. In representative modes of practice, peptides are synthesized in the solid phase using chemistry by which amino acids are added from the C-terminus to the N-terminus. Thus, the amino acid or peptide group proximal to the C-terminus of a particular fragment is the first to be added to the resin. This occurs by reacting the C-terminus functionality of the amino acid or peptide group with complementary functionality on the resin support. The N-terminus side of the amino acid or peptide group is masked to prevent undesired side reactions. The amino acid or peptide group desirably also includes side chain protection as well. Then successive amino acids or peptide groups are attached to the support-bound peptide material until the peptide of interest is formed. Most of these also include side chain protection in accordance with conventional practices. With each successive coupling, the masking group at the N-terminus end of the resin bound peptide material is removed. This is then reacted with the C-terminus of the next amino acid whose N-terminus is masked. The product of solid phase synthesis is thus a peptide bound to a resin support.

Any type of support suitable in the practice of solid phase peptide synthesis can be used. In preferred embodiments, the support comprises a resin that can be made from one or more polymers, copolymers or combinations of polymers such as polyamide, polysulfamide, substituted polyethylenes, polyethyleneglycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can have linkers that are photo-cleavable, TFA-cleavable, HF-cleavable, fluoride ion-cleavable, reductively-cleavable; Pd(O)-cleavable; nucleophilically-cleavable; or radically-cleavable. Preferred linking moieties are cleavable under conditions such that the side-chain groups of the cleaved peptide are still substantially globally protected.

In one preferred method of synthesis, the peptide intermediate fragments synthesized on an acid sensitive solid support that includes trityl groups, and more preferably on a resin that includes trityl groups having pendent chlorine groups, for example a 2-chlorotrityl chloride (2-CTC) resin (Barlos et al. (1989) Tetrahedron Letters 30(30):3943-3946). Examples also include trityl chloride resin, 4-methyltrityl chloride resin, 4-methoxytrityl chloride resin, 4-aminobutan-1-ol 2-chlorotrityl resin, 4-aminomethylbenzoyl 2-chlorotrityl resin, 3-aminopropan-1-ol 2-chlorotrityl resin, bromoacetic acid 2-chlorotrityl resin, cyanoacetic acid 2-chlorotrityl resin, 4-cyanobenzoic acid 2-chlorotrityl resin, glicinol 2-chlorotrityl resin, propionic 2-chlorotrityl resin, ethyleneglycol 2-chlorotrityl resin, N-Fmoc hydroxylamine 2-chlorotrityl resin, hydrazine 2-chlorotrityl resin. Some preferred solid supports include polystyrene, which can be copolymerized with divinylbenzene, to form support material to which the reactive groups are anchored.

Other resins that are used in solid phase synthesis include "Wang" resins, which comprise a copolymer of styrene and divinylbenzene with 4-hydroxymethylphenyloxymethyl anchoring groups (Wang, S. S. 1973, J. Am. Chem. Soc.), and 4-hydroxymethyl-3-methoxyphenoxybutyric acid resin (Richter et al. (1994), Tetrahedron Letters 35(27):4705-4706). The Wang, 2-chlorotrityl chloride, and 4-hydroxymethyl-3-methoxyphenoxy butyric acid resins can be purchased from, for example, Calbiochem-Novabiochem Corp., San Diego, Calif.

In order to prepare a resin for solid phase synthesis, the resin can be pre-washed in suitable solvent(s). For example, a solid phase resin such as a 2-CTC resin is added to a peptide chamber and pre-washed with a suitable solvent. The pre-wash solvent may be chosen based on the type of solvent (or mixture of solvents) that is used in the coupling reaction, or vice versa. Solvents that are suitable for washing, and also the subsequent coupling reaction include dichloromethane (DCM), dichloroethane (DCE), dimethylformamide (DMF), and the like, as well as mixtures of these reagents. Other useful solvents include DMSO, pyridine, chloroform, dioxane, tetrahydrofuran, ethyl acetate, N-methylpyrrolidone, and mixtures thereof. In some cases coupling can be performed in a binary solvent system, such as a mixture of DMF and DCM at a volume ratio in the range of 9:1 to 1:9, more commonly 4:1 to 1:4.

The syntheses of the present invention preferably are carried out in the presence of appropriate protecting groups unless otherwise noted. The nature and use of protecting groups is well known in the art. Generally, a suitable protecting group is any sort of group that can help prevent the atom or moiety to which it is attached, e.g., oxygen or nitrogen, from participating in undesired reactions during processing and synthesis. Protecting groups include side chain protecting groups and amino- or N-terminal protecting groups. Protecting groups can also prevent reaction or bonding of carboxylic acids, thiols and the like.

A side chain protecting group refers to a chemical moiety coupled to the side chain (i.e., R group in the general amino acid formula $H_2N$—$C(R)(H)$—$COOH$) of an amino acid that helps to prevent a portion of the side chain from reacting with chemicals used in steps of peptide synthesis, processing, etc. The choice of a side chain-protecting group can depend on various factors, for example, type of synthesis performed, processing to which the peptide will be subjected, and the desired intermediate product or final product. The nature of the side chain protecting group also depends on the nature of the amino acid itself. Generally, a side chain protecting group is chosen that is not removed during deprotection of the α-amino groups during the solid phase synthesis. Therefore the α-amino protecting group and the side chain protecting group are typically not the same.

In some cases, and depending on the type of reagents used in solid phase synthesis and other peptide processing, an amino acid may not require the presence of a side-chain protecting group. Such amino acids typically do not include a reactive oxygen, nitrogen, or other reactive moiety in the side chain.

Examples of side chain protecting groups include acetyl (Ac), benzoyl (Bz), tert-butyl, triphenylmethyl (trityl), tetrahydropyranyl, benzyl ether (Bzl) and 2,6-dichlorobenzyl (DCB), t-butoxycarbonyl (Boc), nitro, p-toluenesulfonyl (Tos), adamantyloxycarbonyl, xanthyl (Xan), benzyl, 2,6-dichlorobenzyl, methyl, ethyl and t-butyl ester, benzyloxycarbonyl(Z), 2-chlorobenzyloxycarbonyl (2—Cl—Z), Tos, t-amyloxycarbonyl (Aoc), and aromatic or aliphatic urethan-type protecting groups photolabile groups such as nitro veratryl oxycarbonyl (NVOC); and fluoride labile groups such as trimethylsilyl oxycarbonyl (TEOC).

Preferred side chain protecting groups for amino acids commonly used to synthesize Exenatide peptides in the practice of the present invention are shown in the following Table A:

TABLE A

| Amino Acid | Side Chain Protecting group(s) |
|---|---|
| Ala | None |
| Arg | None or pbf* |
| Asp | t-butyl ester (OtBu) |
| Gln | trityl (trt) |
| Glu | OtBu |
| Gly | None |
| His | trityl (trt) |
| Lle | None |
| Leu | None |
| Lys | t-butyloxycarbonyl (Boc) |
| Phe | None |
| Ser | OtBu |
| Thr | tBu |
| Trp | Boc |
| Tyr | tBu |
| Val | None |

*pbf refers to the pentamethyldihydrobenzofuran-5-sulfonyl group. The protected amino acid is N-α-Fmoc-N$^G$-2,2,4,6,7-pentamethyldihydrobenzofuran-5-sulfonyl-L-arginine, and has the formula:

TABLE A-continued

| Amino Acid | Side Chain Protecting group(s) |
|---|---|

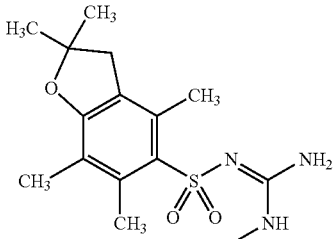

An amino-terminal protecting group includes a chemical moiety coupled to the alpha amino group of an amino acid. Typically, the amino-terminal protecting group is removed in a deprotection reaction prior to the addition of the next amino acid to be added to the growing peptide chain, but can be maintained when the peptide is cleaved from the support. The choice of an amino terminal protecting group can depend on various factors, for example, type of synthesis performed and the desired intermediate product or final product.

Examples of amino-terminal protecting groups include (1) acyl-type protecting groups, such as formyl, acrylyl (Acr), benzoyl (Bz) and acetyl (Ac); (2) aromatic urethane-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic protecting groups such as t-butyloxycarbonyl (Boc), diisopropylmethoxycarbonyl, isopropyloxycarbonyl, ethoxycarbonyl, allyloxycarbonyl; (4) cycloalkyl urethan-type protecting groups, such as 9-fluorenyl-methyloxycarbonyl (Fmoc), cyclopentyloxycarbonyl, adamantyloxycarbonyl, and cyclohexyloxycarbonyl; (5) thiourethan-type protecting groups, such as phenylthiocarbonyl. Preferred protecting groups include 9-fluorenyl-methyloxycarbonyl (Fmoc), 2-(4-biphenylyl)-propyl(2)oxycarbonyl(Bpoc), 2-phenylpropyl(2)-oxycarbonyl (Poc) and t-butyloxycarbonyl (Boc).

Fmoc or Fmoc-like chemistry is highly preferred for solid phase peptide synthesis, inasmuch as cleaving the resultant peptide in a protected state is relatively straightforward to carry out using mildly acidic cleaving agents. This kind of cleaving reaction is relatively clean in terms of resultant by-products, impurities, etc., making it technically and economically feasible to recover peptide on a large scale basis from both the swelling and shrinking washes, enhancing yield. As used herein, "large scale" with respect to peptide synthesis generally includes the synthesis of peptides in the range of at least 500 g, more preferably at least 2 kg per batch. Large-scale synthesis is typically performed in large reaction vessels, such as steel reaction vessels, that can accommodate quantities of reagents such as resins, solvents, amino acids, chemicals for coupling, and deprotection reactions, that are sized to allow for production of peptides in the kilogram to metric ton range.

Additionally, the Fmoc protecting group can be selectively cleaved from a peptide relative to the side chain protecting groups so that the side chain protection are left in place when the Fmoc is cleaved. This kind of selectivity is important during amino acid coupling to minimize side chain reactions. Additionally, the side chain protecting groups can be selectively cleaved to remove them relative to the Fmoc, leaving the Fmoc in place. This latter selectivity is advantageously relied upon during purification schemes described further below.

The solid phase coupling reaction can be performed in the presence of one or more compounds that enhance or improve the coupling reaction. Compounds that can increase the rate of reaction and reduce the rate of side reactions include phosphonium and uronium salts that can, in the presence of a tertiary base, for example, diisopropylethylamine (DIEA) and triethylamine (TEA), convert protected amino acids into activated species (for example, BOP, PyBOPO, HBTU, and TBTU all generate HOBt esters). Other reagents help prevent racemization by providing a protecting reagent. These reagents include carbodiimides (for example, DCC or WSCDI) with an added auxiliary nucleophile (for example, 1-hydroxy-benzotriazole (HOBt), 1-hydroxy-azabenzotriazole (HOAt), or HOSu). The mixed anhydride method, using isobutyl chloroformate, with or without an added auxiliary nucleophile, may also be utilized, as can the azide method, due to the low racemization associated with it. These types of compounds can also increase the rate of carbodiimide-mediated couplings, as well as prevent dehydration of Asn and Gln residues.

After the coupling is determined to be complete, the coupling reaction mixture is washed with a solvent, and the coupling cycle is repeated for each of the subsequent amino acid residues of the peptide material. In order to couple the next amino acid, removal of the N-terminal protecting group (for example, an Fmoc group) from the resin-bound material is typically accomplished by treatment with a reagent that includes 20-50% (on a weight basis) piperidine in a solvent, such as N-methylpyrrolidone (NMP) or dimethylformamide (DMF). After removal of the Fmoc protecting group, several washes are typically performed to remove residual piperidine and Fmoc by-products (such as dibenzofulvene and its piperidine adduct).

The subsequent amino acids can be utilized at a stoichiometric excess of amino acids in relation to the loading factor of peptide material on the resin support. Generally, the amount of amino acids used in the coupling step is at least equivalent to the loading factor of the first amino acid on the resin (1 equivalent or more). Preferably the amount of amino acids used in the coupling step is at least 1.3 equivalent (0.3 excess) or more, and most preferably about 1.5 equivalent (0.5 excess) or more. In some cases, for example, the coupling step utilizes an amount equivalent of amino acids in the range between 1 and 3.

Following the final coupling cycle, the resin is washed with a solvent such as NMP, and then washed with an inert second solvent such as DCM. In order to remove the synthesized peptide material from the resin, a cleaving treatment is carried out in a manner such that the cleaved peptide material still bears sufficient side chain and terminus protecting groups. Leaving the protective groups in place helps to prevent undesirable coupling or other undesirable reactions of peptide fragments during or after resin cleavage. In the case when Fmoc or similar chemistry is used to synthesize the peptide, protected cleavage may be accomplished in any desired fashion such as by using a relatively weak acid reagent such as acetic acid or dilute TFA in a solvent such as DCM. The use of 0.5 to 10 weight percent, preferably 1 to 3 weight percent TFA in DCM is typical. See, e.g., U.S. Pat. No. 6,281,335.

Steps of cleaving the peptide intermediate fragment from the solid phase resin can proceed along the lines of an exemplary process as follows. However, any suitable process that effectively cleaves the peptide intermediate fragment from the resin can be used. For example, approximately 5 to 20, preferably about 10 volumes of a solvent containing an acidic cleaving reagent is added to the vessel containing the resin-bound peptide material. The resin, typically in the form of beads, is immersed in the reagent as a consequence. The cleaving reaction occurs as the liquid contents are agitated at a suitable temperature for a suitable time period. Agitation helps prevent the beads from clumping. Suitable time and temperature conditions will depend upon factors such as the acid reagent being used, the nature of the peptide, the nature of the resin, and the like. As general guidelines, stirring at from about −15° C. to about 5° C., preferably from about −10° C. to about 0° C. for about 5 minutes to two hours, preferably about 25 minutes to about 45 minutes would be suitable. Cleaving time may be in the range of from about 10 minutes to about 2 hours or even as much as a day. Cleaving is desirably carried out in such a chilled temperature range to accommodate a reaction exotherm that might typically occur during the reaction. In addition, the lower temperature of the cleavage reaction prevents acid sensitive side chain protecting groups, such as trt groups, from being removed at this stage.

At the end of the cleaving treatment, the reaction is quenched. This may be achieved, for example, by combining the cleaving reagent with a suitable base, such as pyridine or the like, and continuing to agitate and stir for an additional period such as for an additional 5 minutes to 2 hours, preferably about 20 minutes to about 40 minutes. Adding the base and continued agitation causes the temperature of the vessel contents to increase. At the end of agitation, the vessel contents may be at a temperature in the range of from about 0° C. to about 15° C., preferably about 5° C. to about 10° C.

Factors such as swelling and shrinking the resin in order to improve aspects of the peptide recovery can optionally be incorporated into the overall synthesis process. These techniques are described, for example, in U.S. Pat. Pub. No. 2005/0164912 A1.

In some aspects, the cleaved peptide fragments can be prepared for solution phase coupling to other peptide fragments and/or amino acids. Peptide coupling reactions in the solution phase are reviewed in, for example, *New Trends in Peptide Coupling Reagents*; Albericio, Fernando; Chinchilla, Rafeal; Dodsworth, David J.; and Najera, Armen; Organic Preparations and Procedures International (2003), 33(3), 203-303.

The peptide fragments are preferably isolated before solution phase coupling is undertaken. For instance, according to one illustrative isolation strategy applicable to Fragment 12, Fragment 12 is water extracted one or more times If an emulsion occurs, the present invention employs a brine solution. An illustrative brine solution is a saturated solution of NaCl, desirably filtered to remove solids. The brine solution helps break up the emulsion and gives a better separation layer between DCM and water phases. A back extraction may be used to help achieve higher yields. Distillation is used to reduce the dichloromethane, which is used for cleavage from the resin and at least some subsequent washes followed by heptane addition in order to precipitate the product as a solid for isolation. Any remaining dichloromethane is further reduced by distillation to less than 25 percent by volume. The precipitated Fragment 12 is washed with heptane and then dried under vacuum at a temperature up to 35° C. to conclude the isolation.

In contrast, Fragment 14 may emulsify more easily. Accordingly, water extractions are less desirable as an initial step for isolation of Fragment 14. Instead, an illustrative isolation strategy first reduces dichloromethane (DCM) by distillation, then 25% IPA (Isopropanol) in water is added, and the remaining dichloromethane is further reduced by distillation to less than 25 percent by volume. The precipitated Fragment 14 is isolated, washed with 25% IPA/water, then dried under vacuum at a temperature up to 35° Centigrade.

Isolation of Fragment 16 is similar to that of Fragment 12 in that emulsions of Fragment 16 generally do not form when extracted in water. Therefore, the isolation protocol identified above for Fragment 12 may be followed for Fragment 16.

Coupling of peptide intermediate fragments to other fragments or amino acid(s) in the solution phase can be carried out using in situ coupling reagents, for example, BOP, 6-chloro-1-hydroxybenzotriazole (6-Cl—HOBT), o-(benzotriazol-1-yl)-N,N,N',N'-tetramethyluronium hexafluorophosphate (HBTU), HATU, dicyclohexylcarbodiimide (DCC), water-soluble carbodiimide (WSCDI), or o-(benzotriazol-1-yl)-N,N,N',N'-tetramethyluronium tetrafluoroborate (TBTU). Other coupling techniques use preformed active esters such as hydroxysuccinimide (HOSu) and p-nitrophenol (HONp) esters; preformed symmetrical anhydrides; non-symmetrical anhydrides such as N-carboxyanhydrides (NCAs); or acid halides such as acyl fluoride as well as acyl chloride.

A suitable coupling solvent can be used in the solution phase coupling reaction. It is understood that the coupling solvent(s) used can affect the degree of racemization of the peptide bond formed; the solubility of the peptide and/or peptide fragments; and the coupling reaction rate. In some embodiments, the coupling solvent includes one or more water-miscible reagents. Examples of water-miscible solvents include, for example, DMSO, pyridine, chloroform, dioxane, tetrahydrofuran, ethyl acetate, N-methylpyrrolidone, dimethylformamide (DMF), dioxane, or mixtures thereof.

In other embodiments, the coupling reaction may include one or more non water-miscible reagents. An exemplary non water-miscible solvent is methylene chloride. In these embodiments, the non water-miscible solvent is preferably compatible with the deprotection reaction; for example, if a non water-miscible solvent is used preferably it does not adversely affect the deprotection reaction.

After the peptide 11 is formed, the product can be subject to deprotection, chromatographic purification, lyophilization and/or precipitation, further processing (e.g., reaction with another peptide to form a fusion protein); combinations of these, and/or the like, as desired.

For example, according to the invention, the side-chain protecting groups and some terminus protection groups are typically retained on the peptide intermediate fragments throughout solid phase synthesis and also into and throughout the solution phase coupling reactions. Generally, after solution phase coupling step is completed, one or more deprotection steps may be performed to remove one or more protecting groups from the peptide.

The removal of protecting groups by global deprotection typically utilizes a deprotection solution that includes an acidolytic agent to cleave the side chain protecting groups. Commonly used acidolytic reagents for global deprotection include neat trifluoroacetic acid (TFA), HCl, Lewis acids such as $BF_3Et_2O$ or $Me_3SiBr$, liquid hydrofluoric acid (HF), hydrogen bromide (HBr), trifluoromethanesulfonic acid, and combinations thereof. The deprotection solution also includes one or more suitable cation scavengers, for example, dithiothreitol, anisole, p-cresol, ethanedithiol, or dimethyl sulfide. The deprotection solution can also include water. As used herein, amounts of reagents present in the deprotection composition are typically expressed in a ratio, wherein the amount of an individual component is expressed as a numerator in "parts", such as "parts weight" or "parts volume" and the denominator is the total parts in the composition. For example, a deprotection solution containing TFA:H₂O:DTT in a ratio of 90:5:5 (weight/weight/weight) has TFA at 90/100 parts by weight, H₂O at 5/100 parts by weight, and DTT at 5/100 parts by weight.

In some embodiments, the deprotection reaction can be performed wherein the amount of the acidolytic agent, preferably TFA, in the deprotection composition is greater than 90/100 parts by weight. Other preferred deprotection compositions include an amount of acidolytic agent in an amount of 93/100 parts by weight or greater, or in an amount in the range of 93/100 by weight to 95/100 parts by weight.

The crude solid precipitate may be purified in a variety of ways. According to an illustrative strategy, the crude peptide is dissolved in buffer and purified by reverse phase chromatography. The chromatography fragments are diluted with water and then concentrated on reverse phase chromatography media. After chromatography, the peptide may be isolated using one or more strategies. According to one strategy, conventional lyophilization strategies may be used. Alternatively, precipitation strategies may be used to isolate the peptide. Precipitation is particularly advantageous. Firstly, precipitation is much more economical than lyophilization and is easier to apply at commercial scales. Also, whereas lyophilization provides little if any opportunity to further upgrade the purity of the peptide, precipitation upgrades the peptide purity because salts and other soluble purities stay in solution. Salts in particular are easily washed away. Precipitation provides a purified peptide with very low residual salt content.

A typical chromatographic purification provides the peptide in a liquid medium including water and acetonitrile as main components. Also, TFA counterions tend to be present. To accomplish precipitation, it is desirable to switch the counterion acetate, citrate, succinate, organic carboxylate, and/or the like for formulation. This switch is readily accomplished using a column of reversed phase or ion exchange media. Such a column also tends to concentrate the peptide and changes the solvent system to one more suitable for peptide isolation. A typical resulting solvent is about 4 to about 8 parts by weight ethanol to one part by weight water. After this switching, the eluted fractions from chromatography are precipitated with ethanol, alone or in combination with other alcohols or organic solvents such as ethyl acetate. The precipitate is filtered, then washed with ethanol and dried, packaged, stored, further processed, and/or otherwise handled.

The anhydrous ethanol, absolute or denatured, is added over a period of time such as from about ten to about fifty minutes. This addition occurs mixing/agitation at a controlled temperature such as one in the range of −10° C. to 20° C., as this has been found to yield a peptide that has better filtering characteristics.

The principles of the present invention will now be further illustrated with respect to the following illustrative examples. In the following all percentages and ratios are by volume unless otherwise expressly stated.

Example 1

Solid Phase Synthesis of Fragment 12 with Fmoc Protection at the N-Terminus, Exenatide (1-17) OH A. Preparation of Fmoc-H-Glu-Loaded 2CTC Resin The Fmoc-H-Glu-loaded 2 CTC resin is combined with dichloromethane in order to swell the resin and washed with N,N Dimethylformamide (DMF) (i.e. 10 grams of resin in 60 ml of DMF).

B. Solid Phase Peptide Synthesis of Fragment 12 with Fmoc Protection at the N-Terminus (AA1-17OH)

1. Amino Acid Coupling

The next amino acid loaded onto the H-Glu-resin is Fmoc-L-Glu(tBu)OH. An excess of the protected amino acids (for example, 1.7 to 2.0 equiv), an excess of N-hydroxybenzotriazole (HOBT, for example, 1.7 to 2.0 equiv) and an excess of diisopropylethylamine (DIEA, for example, 1.9 to 2.2 equiv) is combined in DMF and cooled to ≦5° C. The resulting solution is combined with a DMF solution of an excess of 2-(1H-benzotriazole-1-yl) 1,1,3,3-tetramethyluronium hexafluorophosphate (HBTU, for example, 1.7 to 2.0 equiv). This activated amino acid solution is combined with the resin followed by a dichloromethane rinse. The suspension is stirred at ≦25° C. until a negative ninhydrin test (as provided below) is obtained (typically in 3 hours).

| Ninhydrin Test | |
|---|---|
| | Action |
| Negative ninhydrin test | This indicates that the coupling is complete. The liquid is drained and the resin is additionally washed with DMF and process returns to the Fmoc removal step (below) and proceeds through the next amino acid coupling. |
| Positive ninhydrin test | This indicates that the coupling is not complete. If the ninhydrin remains positive, the liquid is drained and the resin is recoupled with 0.5 to 1 equiv of the amino acid and reagents, as previously described. If the ninhydrin is still positive the liquid is drained and the recoupling procedure may be repeated. |

2. Cleavage of the Fmoc and Side-Chain Protected Fragment from the Resin

The Fmoc protecting group is removed by treatment with piperidine (typically 5 to 20%) in DMF solution. The solution is drained and the resin washed with DMF to reduce residual piperidine. The cycle of amino acid coupling and Fmoc removal is repeated for the remaining amino acids in the fragment. All the pseudoproline couplings excluded HOBT. The following protected amino acids are those coupled for this fragment in the order indicated:

Fmoc-L-Glu(tBu)OH
Fmoc-L-MetOH
Fmoc-L-Gln(trt)OH
Fmoc-L-Lys(Boc)OH
Fmoc-L-Leu-Ser(pseudoproline)
Fmoc-L-Asp(tBu)OH
Fmoc-L-Ser(tBu)OH
Fmoc-L-Phe-Thr(pseudoproline)
Fmoc-L-Thr(tBu)OH
Fmoc-L-GlyOH
Fmoc-L-Glu(tBu)OH
Fmoc-L-GlyOH
Fmoc-L-His(trt)OH Following the final coupling, the resin is washed with DMF giving a resin bound, Fmoc-protected Exenatide (1-17) fragment, which may be represented by the notation, FmocAA1-17-resin, having pseudoproline substitutions as noted in the amino acid list above.

The resin-bound FAA1-17OH is cleaved from the resin using dilute (for example, 1%) trifluoroacetic acid (TFA) in dichloromethane for ≦110 min. Pyridine is then added to neutralize the TFA. The liquid is removed and the resin is washed with dichloromethane. The resin-cleavage may be repeated by additional treatment with trifluoroacetic acid in dichloromethane solution, followed by pyridine and the resulting solution combined with the first cleavage solution.

3. Precipitation of FmocAA1-7OH

The Fmoc AA 1-17 OH is water extracted 3 times. Sometimes an emulsion is observed. In such instances, a brine solution (i.e., saturated NaCl in water solution) is used instead of a straight water extraction if emulsions occur. A back extraction (adding DCM to the collection of aqueous extractions) is used to help ensure good yields. Dichloromethane is reduced by distillation. Then, heptane is added as an antisolvent to precipitate the peptide product. Alternatively, a DCM solution of the product may be added to heptane to cause precipitation. The desired order of addition is determined empirically by assessing the properties, i.e., filterability, of the precipitate. Remaining dichloromethane is further reduced by distillation to <25 vol %. The precipitated FAA1-17 OH is isolated, washed with heptane, then dried under vacuum (35° C., max.)

Example 2

Solid Phase Synthesis of Fragment 14 with Fmoc Protection at the N-Terminus, Exenatide(18-26)OH A. Preparation of Fmoc-H-Leu Loaded 2CTC Resin Fmoc-H-Leu loaded 2 CTC Resin is combined with dichloromethane in order to swell the resin and washed with N,N Dimethylformamide (DMF) (i.e. 10 grams of resin in 60 ml of DMF).

B. Solid Phase Peptide Synthesis

1. Amino Acid Coupling

The next amino acid loaded onto the resin is Fmoc-Trp(Boc)OH. An excess of the protected amino acids (for example 1.5 equiv), an excess of N-hydroxybenzotriazole (HOBT, for example 1.5 equiv) and an excess of diisopropylethylamine (DIEA, for example, 1.7 equiv) are combined in DMF and cooled to ≦5° C. The resulting solution is combined with an DMF solution of an excess of 2-(1H-benzotriazole-1-yl) 1,1,3,3-tetramethyluronium hexafluorophosphate (HBTU, for example, 1.5 equiv). The activated amino acid solution is combined with the resin followed by a dichloromethane rinse. The suspension is stirred at ≦25° C. until a negative ninhydrin test (as described above) is obtained (typically 3 h.).

2. Fmoc Removal

The Fmoc protecting group is removed by treatment with piperidine (typically 5 to 20%) in DMF solution. The solution is drained and the resin washed with DMF to reduce residual piperidine.

The cycle of amino acid coupling and Fmoc removal is repeated for the remaining amino acids in the fragment. The following protected amino acids are those coupled for this fragment in the order indicated:
Fmoc-L-Glu(tBu)OH
Fmoc-L-IleOH
Fmoc-L-PheOH
Fmoc-L-LeuOH
Fmoc-L-Arg(pbf)OH
Fmoc-L-ValOH
Fmoc-L-AlaOH Following the final coupling, the resin is washed with DMF giving the Fmoc-protected, resin-bound Exenatide (18-26) fragment which may be identified by the notation FmocAA18-26-resin.

3. Cleavage from the Resin

The resin-bound FmocAA18-26OH is cleaved from the resin using dilute (for example, 2%) trifluoroacetic acid (TFA) in dichloromethane for ≦110 min. Pyridine is added to neutralize the TFA. The solution is removed and the resin washed with dichloromethane. The resin-cleavage may be repeated by additional treatment with trifluoroacetic acid in dichloromethane solution, followed by pyridine.

4. Precipitation of FmocAA18-26 OH

The Fmoc AA 18-26 OH can emulsify easily. Thus, no water extractions are recommended. Instead, dichloromethane is reduced by distillation to <50% of the original volume, 25% IPA (Isopropanol) in water is added, and the remaining dichloromethane is further reduced by distillation to <10 vol %. The precipitated FAA18-26 OH is isolated, washed with 25% IPA/water, then dried under vacuum (35° C., max.)

Example 3

Solid Phase Synthesis of Fragment 16 with Fmoc Protection at the N-Terminus Exenatide(27-38)OH A. Preparation of Fmoc-H-L-Pro Loaded 2CTC Resin The H-L-Pro resin (2-Cl-trityl) is combined with dichloromethane in order to swell the resin and washed with N,N Dimethylformamide (DMF) (i.e. 10 grams of resin in 60 ml of DMF).

B. Solid Phase Peptide Synthesis

1. Amino Acid Coupling

The next amino in the sequence, Fmoc-L-Pro-OH, an excess of the protected amino acids (for example 1.5 equiv), an excess of N-hydroxybenzotriazole (HOBT, for example 1.5 equiv) and an excess of diisopropylethylamine (DIEA, for example, 1.7 equiv) are combined in DMF and cooled to ≦5° C. The resulting solution is combined with a DMF solution of an excess of 2-(1H-benzotriazole-1-yl) 1,1,3,3-tetramethyluronium hexafluorophosphate (HBTU, for example, 1.5 equiv). The activated amino acid solution is combined with the resin, followed by a dichloromethane rinse. The suspension is stirred at ≦25° C., until a negative ninhydrin test (as provided in example 1 above) is obtained (typically 3 h.).

2. Fmoc Removal

The Fmoc protecting group is removed by treatment with piperidine (typically 5 to 20%) in DMF solution. Preferred procedure addition of secondary amine (piperazine+HOBT (i.e. 5 grams piperazine+1.5 g HOBT in 100 ml DMF) especially after second and third Fmoc removal steps). The solution is drained and the resin is washed with DMF to remove residual piperizine.

The cycle of amino acid coupling and Fmoc removal is repeated for the remaining amino acids in the fragment. The cycle is repeated for the remaining amino acids in the fragment. The following protected amino acids are those coupled for this fragment in the order indicated:
Fmoc-L-ProOH
Fmoc-L-AlaOH
Fmoc-L-GlyOH
Fmoc-L-Ser(tBu)OH
Fmoc-L-Ser(tBu)OH
Fmoc-L-ProOH
Fmoc-L-GlyOH
Fmoc-L-GlyOH
Fmoc-L-Asn(trt)OH
Fmoc-L-Lys(Boc)OH
Following the final coupling, the resin is washed with DMF, thus giving the Fmoc-protected, resin-bound Exenatide (27-38) fragment, which may be identified by the notation FmocAA27-38-resin.

3. Cleavage from the Resin

The resin-bound FmocAA27-38OH is cleaved from the resin using dilute (for example, 2%) trifluoroacetic acid (TFA) in dichloromethane for ≦110 min. Pyridine is added to neutralize the TFA. The solution is removed and the resin washed with dichloromethane. The resin-cleavage may be repeated by additional treatment with trifluoroacetic acid in dichloromethane solution, followed by pyridine.

4. Precipitation of FmocAA27-38 OH

The Fmoc AA 27-38 OH is water extracted 3 times. If emulsion is observed a brine solution is recommended as described previously. A back extraction with DCM is used to help ensure good yields. Dichloromethane is reduced by distillation, heptane is added and the remaining dichloromethane is further reduced by distillation to <25 vol %. The precipitated FAA27-38 is isolated, washed with Heptane, then dried under vacuum (35° C., max.).

Example 4

Solution Phase Peptide Synthesis: Adding Serine to Fragment 16

Fragment 16 prepared in Example 3 above can have a Serine amide attached to it by adding (1.2 equiv.), excess 6-chloro-1-hydroxybenzotriazole (6-Cl—HOBT; for example, 1.2-1.4 equiv.), L-Serine(tBu)amide (for example, 1-1.2 equiv.) and DMF. The solution is cooled to ≦5° C. and combined with excess DIEA (for example, 2.0 equiv) and HBTU (for example 1.25 equiv.). The resulting solution is held at ≦0° C., until the reaction is complete (i.e., ≦1% FmocAA27-38OH, e.g., by HPLC). The Fmoc protecting group is then removed. In one approach, piperidine or piperazine bound resin is added to the reaction mixture and the solution is stirred at ≦0° C., until complete (i.e., ≦1% FmocAA27-39NH$_2$, e.g., by HPLC). In another approach, an amine base (e.g., monoethanolamine, dimethylamine, dipropylamine, triethylamine) is added to the reaction mixture and the solution is stirred at ≦0° C., until complete (i.e., ≦1% FmocAA27-39NH$_2$, e.g., by HPLC). The dichloromethane solution is washed with Phosphate buffer (typically pH 8-9). Dichloromethane is reduced by distillation. The cleavage solution is water extracted and then precipitated into a round bottom flask with the MTBE. Alternatively, a DCM solution of the peptide can be added to MTBE to precipitate the peptide. The desired order can be determined empirically by assessing the characteristics of the precipitate formed using each approach Remaining dichloromethane is further reduced by distillation to <25 vol % (e.g., by GC). The precipitated HAA27-39NH$_2$ is isolated, washed with MTBE, then dried under vacuum (35° C., max.). (H at N-terminus refers to amine functionality there. NH$_2$ at C-terminus refers to amide functionality there.)

Example 5

Solution Phase Peptide Synthesis: Preparation of Exenatide(18-39)NH$_2$ (Fragment 22) (NH$_2$ at C-Terminus Refers to Amide Functionality)

H-AA(27-39)NH$_2$ (1.25 equiv), Fmoc-AA(18-26)OH (1 equiv) and an excess of 6-Cl—HOBT (for example, 1.2-1.4 equiv), are dissolved in DCM and DMF (19:1) and the resulting solution is cooled to ≦25° C. The mixture is combined with an excess of N-(3-Dimethylaminopropyl)-N'-ethylcarbodiimide hydrochloride (EDAC) (4 equiv) in DMF. The resulting solution is held at ≦25° C., until the reaction is complete (i.e., ≦1% of total Fmoc-AA(18-26)OH e.g., by HPLC). Additional charges of raw materials and/or reagents may be added if needed. Piperidine or piperazine bound resin is combined with the mixture to remove the Fmoc group (i.e., ≦1% Fmoc-AA(18-39)NH$_2$; e.g. by HPLC). When complete, the mixture is combined with water at ≦25° C. Brine solution as described previously is added to the DCM solution followed by 4 water extractions. This solution is stripped to dryness, and DCM is added back. Dichloromethane is reduced by distillation. Then, either methyl t-butylether (MTBE) is added or DCM is added to the MTBE to precipitate the peptide, and the remaining dichloromethane is further reduced by distillation to <25 vol % (e.g., by GC). The precipitated HAA18-39NH$_2$ is isolated, washed with MTBE, then dried under vacuum (35° C., max.)

Example 6

Solution Phase Peptide Synthesis of Exenatide(1-39)NH$_2$ (Fragment 11) (Fully Protected)

Fragment 22 (Exenatide(18-39)NH$_2$) (1 equiv), Fragment 12 (Exenatide(1-17) as prepared above) (1 equiv), an excess of 6-Cl—HOBT (for example, 1.4-2 equiv), in DCM were combined with an excess of EDAC (for example 3-4 equiv) at ≦0° C. The reaction mixture is stirred until the reaction is complete (i.e., ≦1.0% of AA1-17OH and ≦1.5% of HAA18-39NH$_2$, e.g., by HPLC). Piperidine or piperazine bound resin is added to remove fmoc from the AAF1-39NH2 for a duration of 2 hrs at ≦25° C. The reaction is cooled to 15° C. The reaction is quenched with water and dissolved in DCM. This is then water extracted 4 times and stripped to dryness. The water extraction and FMOC removal steps can be reversed, optionally. The AAH1-39NH2 is dissolved in DCM.

Example 7

Global Deprotection of AA1-39NH$_2$ to Exenatide

The dichloromethane solution from the previous example is combined with trifluoroacetic acid, water and dithiothreitol (for example, 1/0.08/0.012% by weight). The mixture is stirred at ≦24° C. for up to 3 hours, followed by cooling to ≦0° C. The mixture is kept under Nitrogen. Cold MTBE is added dropwise to precipitate the peptide from the reaction mixture. The product slurry is stirred for 1 hr at 0° C. The solids are isolated by filtration, washed with MTBE, and dried under vacuum at ≦35° C.

Example 8

Decarboxylation

IPA, monoethanolamine or, DIEA and Acetic Acid (for example 28:1:1 v/v/v) were premixed and stirred with the deprotected peptide at 35° C. for 3 hrs. The reaction is cooled at 0° C. Filter the HAA1-39NH2 rinse with IPA and dried under vacuum at ≦35° C.

Example 9

Example 9 describes the purification of crude, globally deprotected exenatide by reverse phase chromatography at high pH using Gradient #1.

The following Apparatus are used in Example 9 as described in the Procedure below:
Quaternary pump High Performance Liquid Chromatography (HPLC) system, UV detector, and fraction collector system.

The following Reagents are used in Example 9 as described in the Procedure below:
HPLC Grade Acetonitrile (ACN), Distilled $H_2O$, Ammonium acetate $NH_4OAc$ ACS grade, and Ammonium hydroxide $NH_4OH$ ACS grade.

The Procedure for Example 9 is described as follows:
Step 1. The Mobile Phases A and B were made as follows:
Mobile Phase A was made by mixing 4 g $NH_4OAc$ and 2 mL $NH_4OH$ into 1700 mL $H_2O$. Mixing was performed until the solids dissolved. After mixing, 300 mL ACN was added.
Mobile Phase B was made by mixing 4 g $NH_4OAc$ and 2 mL $NH_4OH$ into 500 mL $H_2O$. Mixing was performed until the solids dissolved. After mixing, 1500 mL ACN was added.
Step 2. Install the column and set the following operating parameters:
Chromatography Conditions:
Column: Kromasil C4 10 μm 2 cm×250 mm
Oven: ambient
Flow rate: 15.5 mL/min
Detector wavelength: VWD: 280 nm
Injection volume: 800 mg contained exenatide/50% sample/50% $H_2O$. As used in this specification, the term "crude" refers to the whole sample. The term "contained" is the amount of exenatide in the whole sample. For example if the crude was 50% pure for every 1 g weighed you would have 0.5 g of actual exenatide.
Run time: 62 minutes+sample load time
Step 3—Filter sample through a 5 μm hydrophobic PTFE filter prior to loading sample into the column.
Step 4—Load sample into the column.
Prior to loading sample, condition column at initial conditions until stable baseline is obtained.

TABLE 1

| | Gradient #1: | | |
|---|---|---|---|
| Time min | Flow mL/min | % A | % B |
| Initial | 15.5 | 100 | 0 |
| Sample load | | 0 | 0 |
| 0.10 | 15.5 | 100.0 | 0.0 |
| 0.20 | 15.5 | 100.0 | 0.0 |
| 1.2 | 15.5 | 100.0 | 0.0 |
| 4.0 | 15.5 | 75.0 | 25.0 |
| 22.0 | 15.5 | 75.0 | 25.0 |
| 22.1 | 15.5 | 0.0 | 100.0 |
| 37.0 | 15.5 | 0.0 | 100.0 |
| 37.1 | 15.5 | 100.0 | 0.0 |
| 52.0 | 15.5 | 100.0 | 0.0 |

Post time (re-equilibration time): 10 min.

Post time (re-equilibration time): 10 min.
Step 5. Collect fractions from 10.0 minutes through 17.5 minutes, 30 to 60 second slices.
Step 6. Fraction pooling criteria: Fractions >97.0% area normalization are collected and pooled for isolation and precipitation. Collect material <97.0% area normalization collect as follows: Fractions collected before the 97.0% fractions are combined as front ends and fractions collected after the 97.0% fractions are combined as back ends. The front ends and back ends are then re-chromatographed as necessary Example 10

Example 10 describes purification of crude, globally deprotected exenatide by reverse phase chromatography at low pH using Gradient #2.

The following Apparatus are used in Example 10 as described in the Procedure below:
Quaternary pump HPLC system, UV detector, and fraction collector system.

The following Reagents are used in Example 10 as described in the Procedure below:
HPLC Grade Acetonitrile (ACN), Distilled $H_2O$, and Trifluoroacetic acid (TFA).

The Procedure for Example 10 is described as follows:
Step 1. The Mobile Phases A and B were made as follows:
Mobile Phase A was made by combining 1802.3 g $H_2O$, 152.0 g ACN, and 3.0 g TFA per 2 liters of mobile phase A (i.e., 1800 mL $H_2O$, 200 mL ACN, 2 mL TFA).
Mobile Phase B was made by combining 1005.2 g $H_2O$, 773.7 g ACN, and 3.0 g TFA per 2 liters of mobile phase B (i.e., 1000 mL $H_2O$, 1000 mL ACN and 2 mL TFA).
Step 2. Install the column and set the following operating parameters:
Chromatography Conditions:
Column: Phenomenex Luna C18 (2) 2 cm×250 mm
Oven: ambient
Flow rate: 5.0 mL/min
Detector wavelength: VWD: 218 nm
Injection volume: 1 g actual crude exenatide/20 mL $H_2O$ (360 mg contained exenatide)
Run time: 60 minutes+sample load time
Sample is filtered through a 5 μm hydrophobic PTFE filter prior to loading sample into the column.
Step 3. Load sample into the column.
Prior to loading sample, condition column at initial conditions until stable baseline is obtained.

TABLE 2

| | | Gradient #2: | |
|---|---|---|---|
| Time min | Flow mL/min | % A | % B |
| Initial | 5.0 | 100 | 0 |
| Sample load | 5.0 | 0 | 0 |
| 0.00 | 5.0 | 90.0 | 10.0 |
| 20.0 | 5.0 | 0 | 100.0 |
| 20.01 | 3.0 | 0 | 100.0 |
| 40.0 | 3.0 | 0 | 100.0 |

Post time: 20 min.

Step 4. Collect fractions from 18.5 minutes through 43.5 minutes. 15 second slices were taken through the apex of the peak and 30 to 60 second slices were taken on the front side and the back side of the apex.
4. Pool fractions as follows: ≦85% area normalization for front ends and back ends and pool ≧85% for purification on the high pH column.

Example 11

Example 11 describes the purification of crude, globally deprotected exenatide by reverse phase chromatography at low pH using Gradient #3.
The following Apparatus are used in Example 11 as described in the Procedure below:
Quaternary pump HPLC system, UV detector, and fraction collector system.
The following Reagents are used in Example 11 as described in the Procedure below:
HPLC Grade Acetonitrile (ACN), Distilled $H_2O$, Tetrahydrofuran (THF), Trifluoroacetic acid (TFA), Glacial acetic acid HPLC, U.S.P. or ACS grade, Sodium acetate trihydrate HPLC, U.S.P. or ACS grade and L-Methionine 98%+ or equivalent.
The Procedure for Example 11 is described as follows:
Step 1. The Mobile Phases A and B were made as follows:
Mobile Phase A was made by combining 1802.3 g $H_2O$, 152.0 g ACN, and 3.0 g TFA per 2 liters of mobile phase A (i.e., 1800 mL $H_2O$, 200 mL ACN, 2 mL TFA).
Mobile Phase B was made by combining 1005.2 g $H_2O$, 531.4 g ACN, 261.5 g THF, and 3.0 g TFA per 2 liters of mobile phase B (i.e., 1000 mL $H_2O$, 700 mL ACN, 300 mL THF, and 2 mL TFA).
Note: THF was peroxide free.
Peroxide Scavenger Solution Preparation:
1.63 g sodium acetate trihydrate, 1.49 g L-methionine, and 1.08 g acetic acid added to 1000 mL $H_2O$.
Step 2. Install the column and set the following operating parameters:
Chromatography Conditions:
Column: Kromasil 100-10-C18 1 cm×250 mm
Oven: ambient
Flow rate: 3.6 mL/min
Detector wavelength: VWD: 280 nm
Injection volume: 100 mg contained exenatide/20 mL, mobile phase A
Run time: 50 minutes+sample load time
Step 3. Filter sample through a 5 μm hydrophobic PTFE filter prior to loading sample into the column.
Step 4. Load sample into the column.
Prior to loading sample, condition column at initial conditions until stable baseline is obtained.

TABLE 3

| | | Gradient #3: | |
|---|---|---|---|
| Time min | Flow mL/min | % A | % B |
| Initial | 3.6 | 100 | 0 |
| Sample load | 3.6 | 0 | 0 |
| 0.01 | 3.6 | 70.0 | 30.0 |
| 24.0 | 3.6 | 22.0 | 78.0 |
| 24.01 | 3.6 | 22.0 | 78.0 |
| 24.10 | 3.6 | 0.0 | 100.0 |
| 40.0 | 3.6 | 0.0 | 100.0 |

Post time: 20 min.

Step 5. Collect fractions from 16.0 minutes through 22.0 minutes, 15 to 30 second slices.
Step 6. Add equal volume of scavenger solution to each fraction collected, store under $N_2$ and at 0-6° C.
Step 7. Pool fractions as follows: ≦85.0% area normalization for front ends and back ends and pool ≧85.0% for purification on the high pH column.

Example 12

Example 12 describes the purification of crude, globally deprotected exenatide by reverse phase chromatography at low pH using Gradient #4.
The following Apparatus are used in Example 12 as described in the Procedure below:
Quaternary pump HPLC system, UV detector, and fraction collector system.
The following Reagents are used in Example 12 as described in the Procedure below:
HPLC Grade Acetonitrile (ACN), Distilled $H_2O$, and Trifluoroacetic acid (TFA).
The Procedure for Example 12 is described as follows:
Step 1. The Mobile Phases A and B were made as follows:
Mobile Phase A was made by combining 1802.3 g $H_2O$, 152.0 g ACN, and 3.0 g TFA per 2 liters of mobile phase A (i.e., 1800 mL $H_2O$, 200 mL ACN, 2 mL TFA).
Mobile Phase B was made by combining 1005.2 g $H_2O$, 773.7 g ACN, and 3.0 g TFA per 2 liters of mobile phase B (i.e., 1000 mL $H_2O$, 1000 mL ACN, and 2 mL TFA).
Step 2. Install the column and set the following operating parameters:
Chromatography Conditions:
Column: Kromasil 100-10-C18 1 cm×250 mm
Oven: ambient
Flow rate: 3.6 mL/min
Detector wavelength: VWD: 280 nm
Injection volume: 100 mg contained exenatide/20 mL, mobile phase A
Run time: 50 minutes+sample load time
Step 3. Filter sample through a 5 μm hydrophobic PTFE filter prior to loading sample into the column.
Step 4. Load sample into the column.
Prior to loading sample, condition column at initial conditions until stable baseline is obtained.

TABLE 4

| | | Gradient #4: | |
|---|---|---|---|
| Time min | Flow mL/min | % A | % B |
| Initial | 3.6 | 100 | 0 |
| Sample load | 3.6 | 0 | 0 |

TABLE 4-continued

| Gradient #4: | | | |
|---|---|---|---|
| Time min | Flow mL/min | % A | % B |
| 0.01 | 3.6 | 78.0 | 22.0 |
| 14.0 | 3.6 | 22.0 | 78.0 |
| 14.01 | 3.6 | 22.0 | 78.0 |
| 14.10 | 3.6 | 0.0 | 100.0 |
| 30.0 | 3.6 | 0.0 | 100.0 |

Post time: 20 min.

Step 5. Collect fractions from 14.0 minutes through 24.0 minutes, 15 to 30 second slices.
Step 6. Pool fractions as follows: ≦85.0% area normalization for front ends and back ends and pool ≧85.0% for purification on the high pH column.

Example 13

Solid Phase Peptide Synthesis of Exenatide(1-19)

A. Preparation of Fmoc-L-Val Loaded Resin
The Fmoc L Valine resin (2-Cl-trityl) (1 equiv) is combined with dichloromethane in order to swell the resin and washed with N,N Dimethylformamide (DMF). (i.e. 10 grams of resin in 60 ml of DMF).

B. Solid Phase Synthesis
1. Amino Acid Coupling for F(1-19)
The next amino acid loaded onto the H-Val-resin is Fmoc-L-Ala OH. An excess of the protected amino acids (for example, 1.7 to 2.0 equiv), an excess of N-hydroxybenzotriazole (HOBT, for example, 1.7 to 2.0 equiv) and an excess of diisopropylethylamine (DIEA, for example, 1.9 to 2.2 equiv) is combined in DMF and cooled to ≦5° C. The resulting solution is combined with an DMF solution of an excess of 2-(1H-benzotriazole-1-yl) 1,1,3,3-tetramethyluronium hexafluorophosphate (HBTU, for example, 1.7 to 2.0 equiv). This activated amino acid solution is combined with the resin followed by a dichloromethane rinse. The suspension is stirred at ≦25° C. until a negative ninhydrin test (as described above) is obtained (typically 3 h.).

2. Fmoc Removal
The Fmoc protecting group is removed by treatment with piperidine (typically 5 to 20%) in DMF solution. The solution is drained and the resin washed with DMF to reduce residual piperidine.

The cycle of amino acid coupling and Fmoc removal is repeated for the remaining amino acids in the fragment. All the pseudoproline couplings excluded HOBT. The following protected amino acids are those coupled for this fragment in the order indicated:
Fmoc-L-Glu(tBu)OH
Fmoc-L-Glu(tBu)OH
Fmoc-L-Glu(tBu)OH
Fmoc-L-MetOH
Fmoc-L-Gln(trt)OH
Fmoc-L-Lys(Boc)OH
Fmoc-L-Leu-Ser(pseudoproline)
Fmoc-L-Asp(tBu)OH
Fmoc-L-Ser(tBu)OH
Fmoc-L-Phe-Thr(pseudoproline)
Fmoc-L-Thr(tBu)OH
Fmoc-L-GlyOH
Fmoc-L-Glu(tBu)OH
Fmoc-L-GlyOH
Fmoc-L-His(trt)OH Following the final coupling, the resin is washed with DMF giving the Fmoc-protected, resin-bound Exenatide (1-19) fragment, which may be identified by the notation FmocAA1-19-resin, have pseudoproline substitutions as noted in the amino acid list above.

3. Cleavage from the Resin
The resin-bound FAA1-19OH is cleaved from the resin using dilute (for example, 1%) trifluoroacetic acid (TFA) in dichloromethane for ≦110 min. Pyridine is then added to neutralize the TFA. The liquid is removed and the resin is washed with dichloromethane. The resin-cleavage may be repeated by additional treatment with trifluoroacetic acid in dichloromethane solution, followed by pyridine and the resulting solution combined with the first cleavage solution.

4. Precipitation of FmocAA1-19 OH
The Fmoc AA 1-19 OH is water extracted 3 times. If emulsion is observed a brine solution is recommended. A back extraction with DCM is used to help ensure good yields. Dichloromethane is reduced by distillation, heptane is added to precipitate the peptide, and the remaining dichloromethane is further reduced by distillation to <25 vol %. The precipitated FAA1-19 is isolated, washed with heptane, then dried under vacuum (35° C., max.)

Example 14

Solid Phase Peptide Synthesis of Fmoc Protected Exenatide(20-29)

A. Preparation of Fmoc-H-Gly-Loaded Resin
The H-Gly-resin (2-Cl-trityl) (1 equiv) is combined with dichloromethane in order to swell the resin and washed with N,N Dimethylformamide (DMF). (i.e. 10 grams of resin in 60 ml of DMF).

B. Solid Phase Synthesis
1. Amino Acid Coupling
The next amino acid loaded onto the resin is Fmoc-Asn(trt)OH. An excess of the protected amino acids (for example 1.5 equiv), an excess of 6 Cl N-hydroxybenzotriazole (6 Cl HOBT, for example 1.5 equiv) and an excess of N,N-diisopropylcarbodiimide (DIC, for example, 1.7 equiv) are combined in DMF:DMSO Dimethyl sulfoxide (1:1) and cooled to ≦25° C. The activated amino acid solution is combined with the resin followed by a dichloromethane rinse. The suspension is stirred at ≦25° C. until a negative ninhydrin test (described above) is obtained (typically 3 h.)

2. Fmoc Removal
The Fmoc protecting group is removed by treatment with piperidine (typically 5 to 20%) in DMF solution. The solution is drained and the resin washed with DMF to reduce residual piperidine.

The cycle of amino acid coupling and Fmoc removal is repeated for the remaining amino acids in the fragment. The following protected amino acids are those coupled for this fragment in the order indicated:
Fmoc-Lys(Boc)OH
Fmoc-LeuOH
Fmoc-L-Trp(Boc)OH
Fmoc-L-Glu(tBu)OH
Fmoc-L-IleOH
Fmoc-L-PheOH
Fmoc-L-LeuOH
Fmoc-L-Arg(Pbf)OH Following the final coupling, the resin is washed with DMF giving the Fmoc-protected, resin-bound Exenatide (20-29) fragment, which may be identified by the notation FmocAA20-29-resin.

3. Cleavage from the Resin

The resin-bound FmocAA20-29OH is cleaved from the resin using dilute (for example, 2%) trifluoroacetic acid (TFA) in dichloromethane for ≦110 min. Pyridine is added to neutralize the TFA. The solution is removed and the resin washed with dichloromethane. The resin-cleavage may be repeated by additional treatment with trifluoroacetic acid in dichloromethane solution, followed by pyridine.

4. Precipitation of FmocAA20-29 OH

The Fmoc AA20-29 OH can emulsify easily. Thus, no water extractions are recommended. Instead, dichloromethane is reduced by distillation, 25% IPA (Isopropanol) in water is added, and the remaining dichloromethane is further reduced by distillation to <25 vol %. The precipitated FAA20-29 OH is isolated, washed with 25% IPA/water, then dried under vacuum (35° C., max.)

Example 15

Solid Phase Peptide Synthesis of Exenatide(30-38)

A. Preparation of H-L-Pro-Loaded Resin

The H-L-Pro resin (2-Cl-trityl) (1 equiv) is combined with dichloromethane in order to swell the resin and washed with N,N Dimethylformamide (DMF). (i.e. 10 grams of resin in 60 ml of DMF).

B. Solid Phase Synthesis

1. Amino Acid Coupling

The next amino in the sequence, Fmoc-L-Pro-OH, an excess of the protected amino acids (for example 1.5 equiv), an excess of N-hydroxybenzotriazole (HOBT, for example 1.5 equiv) and an excess of diisopropylethylamine (DIEA, for example, 1.7 equiv) are combined in DMF and cooled to ≦5° C. The resulting solution is combined with a DMF solution and an excess of 2-(1H-benzotriazole-1-yl) 1,1,3,3-tetramethyluronium hexafluorophosphate (HBTU, for example, 1.5 equiv). The activated amino acid solution is combined with the resin, followed by a dichloromethane rinse. The suspension is stirred at ≦25° C., until a negative ninhydrin test as described above is obtained (typically 3 h.).

2. Fmoc Removal

The Fmoc protecting group is removed by treatment with piperidine (typically 5 to 20%) in DMF solution except for the second and third Pro in which case piperazine is used. The solution is drained and the resin is washed with DMF to remove residual base.

The cycle of amino acid coupling and Fmoc removal is repeated for the remaining amino acids in the fragment. The cycle is repeated for the remaining amino acids in the fragment. The following protected amino acids are those coupled for this fragment in the order indicated:

Fmoc-L-ProOH
Fmoc-L-AlaOH
Fmoc-L-GlyOH
Fmoc-L-Ser(tBu)OH
Fmoc-L-Ser(tBu)OH
Fmoc-L-ProOH
Fmoc-L-GlyOH Following the final coupling, the resin is washed with DMF and then dichloromethane giving the Fmoc-protected, resin-based Exenatide (30-38) fragment, which may be identified by the notation FmocAA30-38-resin.

3. Cleavage from the Resin

The resin-bound FmocAA30-38OH is cleaved from the resin using dilute (for example, 2%) trifluoroacetic acid (TFA) in dichloromethane for ≦110 min. Pyridine is added to neutralize the TFA. The solution is removed and the resin washed with dichloromethane. The resin-cleavage may be repeated by additional treatment with trifluoroacetic acid in dichloromethane solution, followed by pyridine.

4. Precipitation of Fragment

The Exenatide(30-38)OH is water extracted 3 times. If emulsion is observed a brine solution is recommended. A back extraction with DCM is used to ensure good yields. Dichloromethane is reduced by distillation, heptane is added and the remaining dichloromethane is further reduced by distillation to <25 vol %. The precipitated FAA30-38 is isolated, washed with Heptane, then dried under vacuum (35° C., max.)

Example 16

Solution Phase Peptide Synthesis of Exenatide(30-39)NH$_2$

FmocAA30-38OH (1.2 equiv.), excess 6-chloro-1-hydroxybenzotriazole (6-Cl—HOBT; for example, 1.2-1.4 equiv.), L-Serine(tBu)amide (for example, 1-1.2 equiv.) and DCM are combined. The solution is cooled to ≦5° C. and combined with excess DIEA (for example, 2.0 equiv) and HBTU (for example 1.2 equiv.). The resulting solution is held at ≦0° C., until the reaction is complete (i.e., ≦1% FmocAA27-38OH, e.g., by HPLC). The reaction mixture is combined with dilute aqueous acetic acid (typically 3% to 5%) at 25 degrees. The dichloromethane solution is washed with dilute aqueous sodium bicarbonate (typically 2 to 3%) and 2 water washes are then stripped to an oil. Back extraction is recommended with dichloromethane. In order to remove the Fmoc protecting group, piperidine or piperazine bound resin is added to the reaction mixture and the solution is stirred at ≦0° C., until complete (i.e., ≦1% FmocAA30-39NH$_2$, e.g., by HPLC). Dichloromethane is reduced by distillation, methyl t-butylether (MTBE) is added to precipitate the peptide, and the remaining dichloromethane is further reduced by distillation to <25 vol % (eg., by GC). The precipitated HAA30-39NH$_2$ is isolated, washed with MTBE, then dried under vacuum (35° C., max.)

Example 17

Solution Phase Peptide Synthesis of Exenatide(20-39)NH$_2$

H-AA(30-39)NH$_2$ (1.25 equiv), Fmoc-AA(20-29)OH (1 equiv) and an excess of 6-Cl—HOBT (for example, 1.2-1.4 equiv), are dissolved in DCM. The solution is cooled to ≦25° C. and combined with excess DIEA (for example, 2.7 equiv) and HBTU (for example 1.2 equiv.). The resulting solution is held at ≦25° C., until the reaction is complete (i.e., ≦1% of total Fmoc-AA(20-29)OH e.g., by HPLC). Additional charges of raw materials and/or reagents may be added if needed. Piperidine or piperazine bound resin is combined with the mixture to remove the Fmoc group (i.e., ≦1% Fmoc-AA(20-39)NH$_2$; e.g. by HPLC). When complete, the mixture is combined with a brine wash and then 4× water washes at ≦25° C. A Back extraction with dichloromethane is used to increase yield. Dichloromethane is reduced by distillation, methyl t-butylether (MTBE) is added and the remaining dichloromethane is further reduced by distillation to <25 vol % (eg., by GC). The precipitated HAA20-39NH$_2$ is isolated, washed with MTBE, then dried under vacuum (35° C., max.)

Example 18

Solution Phase Peptide Synthesis of Exenatide(1-39)NH$_2$ (Fully Protected)

HAA20-39NH$_2$ (1 equiv), AAF1-19OH (1 equiv), an excess of 6-Cl—HOBT (for example, 1.5-2 equiv), in DCM are combined with an excess of HBTU and DIEA at ≦0° C. The reaction mixture is stirred until the reaction is complete (i.e., ≦1.0% of AA1-19OH and ≦1.5% of HAA20-39NH$_2$, e.g., by HPLC). Cool the reactor to 15° C., quench with DCM, and warm to 25° C. Water extract 2 times with water. Concentrate the DCM layer. Piperidine or piperazine bound resin is added to remove Fmoc to provide the AAF1-39NH2 for a duration of 2 hrs at ≦25° C. The AAH1-39NH2 is dissolved in DCM. An alternative route is to use DIC(N,N'-Diisopropylcarbodiimide) in DMF instead of the HBTU/DIEA 5 minutes before one is to activate the reaction, cool the reaction to 0° C. After activation wait 5 minutes. Then warm up the sample to room temperature (25° C.). Doing water extractions and then removing Fmoc protection can increase the wt/wt value. One can also try the Fmoc removal, and then performing a water extraction.

Example 19

Global Deprotection of Exenatide(1-39)NH$_2$

The dichloromethane solution from the previous step is combined with trifluoroacetic acid, water and dithiothreitol (for example, 1/0.08/0.012 ratio). The mixture is stirred at ≦24° C. for up to 3 hours, followed by cooling to ≦0° C. Keep under Nitrogen at all times. Cold MTBE is added to precipitate the peptide from the reaction mixture dropwise. Once all the peptide is in the MTBE stir for 1 hr. The solids are isolated by filtration, washed with MTBE and partially dried under vacuum at ≦35° C.

Example 20

Decarboxylation

The protocol outlined in Example 8 above was followed to decarboxylate the deprotected peptide of Example 19.

Example 21

Purification

The protocol outlined in any of Examples 9-12 above is followed, respectively, to purify the decarboxylated peptide of Example 20.

Example 22

Concentration and Isolation Performed after Chromatography

All solutions should be de-oxygenated by sparging with Nitrogen for at least 10 minutes prior to use. Keep all solutions with product under Nitrogen. All operations, except as noted, are done at room temperature.
1. Adjust peptide solution to <10% acetonitrile (ACN) by Karl Fischer titration. All pool fractions are diluted with two volumes of water. This provides the correct ACN concentration. A vacuum distillation may also be used to remove acetonitrile.
2. Load Amberchrome column (see preparation of column below) at about 2 ml/min.
3. Wash with 1 column volume of 0.5 M (38.5 g/l) ammonium acetate at about 4 ml/min to remove HPLC buffer.
4. Wash with 1 column volume of 2-5% by weight acetic acid solution at about 4 ml/min.
5. Wash with 1 column volume of water at about 4 ml/min.
6. Elute with 80:20 (wt/wt) EtOH (2B): water at a flow rate of about 2 ml/min.
7. Collect fractions. Peptide should elute immediately after the void volume. The ethanol concentration may be increased during the elution, or the tail may be collected separately for re-injection with the next run.
8. Column can be regenerated by flushing with 4 column volumes of water.
9. Further concentration can be performed by distilling off the ethanol/water azeotrope.
10. Add ethanol (2B) with agitation to product fraction to precipitate peptide. About 10-15 volumes of ethanol are used for the precipitation.
11. Cool with agitation to <0° C. and hold for at least 2 hours.
12. An organic co-solvent such as toluene, MTBE or ethyl acetate may be used to enhance the yield of the precipitation.
13. Pressure filter using nitrogen pressure through a nominal 1 μm filter membrane. Recycle first portion if it is cloudy. Keep filter cold
14. Rinse with 10 ml/gram EtOH (2B or absolute ethanol can be used). Continue blowing nitrogen until dry. Filter may be warmed to 25° C. during drying.
15. Continue drying under reduced pressure until desired residual solvent level is achieved.
16. Sample for residual solvent before digging out filter and packaging.

Preparation of Amberchrome Column:
1. The Amberchrome comes as a 50% slurry in ethanol. Define the slurry at least once prior to loading.
2. Settle for 30 min and decant off fines. Add back an equal volume of water.
3. Pour slurry into column. Open valve and drain off excess liquid.
4. Wash column with two column volumes of water.
5. Drain down any liquid above resin bed prior to loading.

Example 23

The following is an example of exenatide performed after chromatography. A 2.5×17 cm Amberchrome CM resin is packed in a low pressure glass column and equilibrated with de-ionized water. The purified peptide solution containing 4.7 g purified peptide in a volume of 950 ml is loaded onto the column at a rate up to 4 ml per minute. The peptide solution should be diluted to a water concentration of greater than 90%. When loaded, the peptide bound resin is washed with 120 ml 0.1 M aqueous ammonium acetate solution followed by 120 ml of a 2% aqueous acetic acid solution. The peptide is then eluted with a solution of 5:1 ethanol water and product containing fractions are collected. The collected concentrate solution of about 150 ml is then precipitated by the addition of 800 ml ethanol at a rate of about 30 ml per minute. The slurry is then cooled to −20° C. and held for 2 hours. The precipitation is completed by the addition of 70 ml ethyl acetate and holding an additional 30 minutes. The slurry is filtered through a fritted glass funnel and washed with 200 ml ethanol. The wet cake is dried under a stream of nitrogen and reduced pressure at room temperature until fully dry. This yielded 3.8 grams of dried, purified peptide.

What is claimed is:

1. A peptide derivative, comprising:
a non-resin bound peptide comprising at least two repeating glutamic acid residues in direct sequence (Glu-Glu); and a residue of at least one pseudoproline moiety, wherein the peptide derivative is a partially or wholly protected peptide.

2. The peptide derivative of claim 1, wherein at least a first pseudoproline moiety is between the repeating sequence of glutamic acid residues and the N-terminus of the peptide.

3. The peptide derivative of claim 2, wherein there are at least two amino acid residues between the first pseudoproline moiety and the closest Glu residue of the repeating sequence of glutamic acid residues.

4. A peptide derivative, comprising:
a peptide comprising at least two repeating glutamic acid residues in direct sequence (Glu-Glu); and a residue of at least one pseudoproline moiety, wherein the peptide derivative is a partially or wholly protected peptide and wherein at least a first pseudoproline moiety is between the repeating sequence of glutamic acid residues and the N-terminus of the peptide; said peptide further comprising a second pseudoproline moiety downstream from the first pseudoproline moiety.

5. The peptide derivative of claim 4, wherein the peptide comprises at least 15 amino acid.

6. The peptide derivative of claim 4, wherein the peptide comprises up to 21 amino acids.

7. The peptide derivative of claim 4, wherein no more than two amino acid residues are between the repeating sequence of glutamic acid residues and the C-terminus of the fragment.

8. The peptide derivative of claim 4, wherein the repeating sequence of glutamic acid residues is the C-terminus of the fragment.

9. The peptide derivative of claim 4, wherein the peptide is comprised of at least three glutamic acid residues in direct sequence (Glu-Glu-Glu).

10. A peptide derivative, comprising:
a peptide comprising at least two repeating glutamic acid residues in direct sequence (Glu-Glu); and a residue of at least one pseudoproline moiety, wherein the peptide derivative is a partially or wholly protected peptide and wherein at least a first pseudoproline moiety is between the repeating sequence of glutamic acid residues and the N-terminus of the peptide derivative, wherein the peptide is selected from the group consisting of:

SEQ ID No. 2:
His-Gly-Glu-Gly-Thr-$X^6$-$X^7$-Ser-Asp-Leu-Ser-Lys-Gln-Met-Glu-Glu-Glu-Ala-Val;

SEQ ID No. 3:
His-Gly-Glu-Gly-Thr-Phe-Thr-Ser-Asp-$X^{10}$-$X^{11}$-Lys-Gln-Met-Glu-Glu-Glu-Ala-Val;

SEQ ID No. 4:
His-Gly-Glu-Gly-Thr-$X^6$-$X^7$-Ser-Asp-$X^{10}$-$X^{11}$-Lys-Gln-Met-Glu-Glu-Glu-Ala-Val;

SEQ ID No.5:
His-Gly-Glu-$X^4$-$X^5$-Phe-Thr-Ser-Asp-Leu-Ser-Lys-Gln-Met-Glu-Glu-Glu-Ala-Val;

SEQ ID No. 6:
His-Gly-Glu-$X^4$-$X^5$-Phe-Thr-Ser-Asp-$X^{10}$-$X^{11}$-Lys-Gln-Met-Glu-Glu-Glu-Ala-Val;

SEQ ID No. 7:
His-Gly-Glu-$X^4$-$X^5$-Phe-$X^7$-$X^8$-Asp-Leu-Ser-Lys-Gln-Met-Glu-Glu-Glu-Ala-Val;

SEQ ID No. 8:
His-Gly-Glu-$X^4$-$X^5$-$X^6$-$X^7$-Ser-Asp-Leu-Ser-Lys-Gln-Met-Glu-Glu-Glu-Ala-Val;

SEQ ID No. 9:
His-Gly-Glu-Gly-Thr-Phe-$X^7$-$X^8$-Asp-Leu-Ser-Lys-Gln-Met-Glu-Glu-Glu-Ala-Val;

SEQ ID No. 10:
His-Gly-Glu-Gly-Thr-Phe-$X^7$-$X^8$-Asp-$X^{10}$-$X^{11}$-Lys-Gln-Met-Glu-Glu-Glu-Ala-Val;

SEQ ID No. 11:
His-Gly-Glu-$X^4$-$X^5$-Phe-$X^7$-$X^8$-Asp-$X^{10}$-$X^{11}$-Lys-Gln-Met-Glu-Glu-Glu-Ala-Val;

SEQ ID No. 12:
His-Gly-Glu-Gly-Thr-$X^6$-$X^7$-Ser-Asp-Leu-Ser-Lys-Gln-Met-Glu-Glu-Glu-Ala;

SEQ ID No. 13:
His-Gly-Glu-Gly-Thr-Phe-Thr-Ser-Asp-$X^{10}$-$X^{11}$-Lys-

Gln-Met-Glu-Glu-Glu-Ala;

SEQ ID No. 14:
His-Gly-Glu-Gly-Thr-$X^6$-$X^7$-Ser-Asp-$X^{10}$-$X^{11}$-Lys-Gln-

Met-Glu-Glu-Glu-Ala;

SEQ ID No. 15:
His-Gly-Glu-$X^4$-$X^5$-Phe-Thr-Ser-Asp-Leu-Ser-Lys-Gln-

Met-Glu-Glu-Glu-Ala;

SEQ ID No. 16:
His-Gly-Glu-$X^4$-$X^5$-Phe-Thr-Ser-Asp-$X^{10}$-$X^{11}$-Lys-Gln-

Met-Glu-Glu-Glu-Ala;

SEQ ID No. 17:
His-Gly-Glu-$X^4$-$X^5$-Phe-$X^7$-$X^8$-Asp-Leu-Ser-Lys-Gln-

Met-Glu-Glu-Glu-Ala;

SEQ ID No. 18:
His-Gly-Glu-$X^4$-$X^5$-$X^6$-$X^7$-Ser-Asp-Leu-Ser-Lys-Gln-

Met-Glu-Glu-Glu-Ala;

SEQ ID No. 19:
His-Gly-Glu-Gly-Thr-Phe-$X^7$-$X^8$-Asp-Leu-Ser-Lys-Gln-

Met-Glu-Glu-Glu-Ala;

SEQ ID No. 20:
His-Gly-Glu-Gly-Thr-Phe-$X^7$-$X^8$-Asp-$X^{10}$-$X^{11}$-Lys-Gln-

Met-Glu-Glu-Glu-Ala;

SEQ ID No. 21:
His-Gly-Glu-$X^4$-$X^5$-Phe-$X^7$-$X^8$-Asp-$X^{10}$-$X^{11}$-Lys-Gln-

Met-Glu-Glu-Glu-Ala;

SEQ ID No. 22:
His-Gly-Glu-Gly-Thr-$X^6$-$X^7$-Ser-Asp-Leu-Ser-Lys-Gln-

Met-Glu-Glu-Glu;

SEQ ID No. 23:
His-Gly-Glu-Gly-Thr-Phe-Thr-Ser-Asp-$X^{10}$-$X^{11}$-Lys-

Gln-Met-Glu-Glu-Glu;

SEQ ID No. 24:
His-Gly-Glu-Gly-Thr-$X^6$-$X^7$-Ser-Asp-$X^{10}$-$X^{11}$-Lys-Gln-

Met-Glu-Glu-Glu;

SEQ ID No. 25:
His-Gly-Glu-$X^4$-$X^5$-Phe-Thr-Ser-Asp-Leu-Ser-Lys-Gln-

Met-Glu-Glu-Glu;

SEQ ID No. 26:
His-Gly-Glu-$X^4$-$X^5$-Phe-Thr-Ser-Asp-$X^{10}$-$X^{11}$-Lys-Gln-

Met-Glu-Glu-Glu;

SEQ ID No. 27:
His-Gly-Glu-$X^4$-$X^5$-Phe-$X^7$-$X^8$-Asp-Leu-Ser-Lys-Gln-

Met-Glu-Glu-Glu;

SEQ ID No. 28:
His-Gly-Glu-$X^4$-$X^5$-$X^6$-$X^7$-Ser-Asp-Leu-Ser-Lys-Gln-

Met-Glu-Glu-Glu;

SEQ ID No. 29:
His-Gly-Glu-Gly-Thr-Phe-$X^7$-$X^8$-Asp-Leu-Ser-Lys-Gln-

Met-Glu-Glu-Glu;

SEQ ID No. 30:
His-Gly-Glu-Gly-Thr-Phe-$X^7$-$X^8$-Asp-$X^{10}$-$X^{11}$-Lys-Gln-

Met-Glu-Glu-Glu;
and

SEQ ID No. 31:
His-Gly-Glu-$X^4$-$X^5$-Phe-$X^7$-$X^8$-Asp-$X^{10}$-$X^{11}$-Lys-Gln-

Met-Glu-Glu-Glu;

wherein in SEQ ID Nos. 2 through 31 $X^4$-$X^5$ at positions 4 and 5; $X^6$-$X^7$ at positions 6 and 7; $X^7$-$X^8$ at positions 7 and 8; and $X^{10}$-$X^{11}$ at positions 10 and 11 comprise a pseudoproline.

11. The peptide derivative of claim 10, wherein the peptide has the sequence:

SEQ ID No. 24:
His-Gly-Glu-Gly-Thr-$X^6$-$X^7$-Ser-Asp-$X^{10}$-$X^{11}$-Lys-Gln-

Met-Glu-Glu-Glu.

12. The peptide derivative of claim 10, wherein the peptide is selected from the group consisting of:

SEQ ID No. 22:
His-Gly-Glu-Gly-Thr-$X^6$-$X^7$-Ser-Asp-Leu-Ser-Lys-Gln-

Met-Glu-Glu-Glu;
and

SEQ ID No. 23:
His-Gly-Glu-Gly-Thr-Phe-Thr-Ser-Asp-$X^{10}$-$X^{11}$-Lys-

Gln-Met-Glu-Glu-Glu.

13. The peptide derivative of claim 10, wherein the peptide has the sequence:

SEQ ID No. 14:
His-Gly-Glu-Gly-Thr-$X^6$-$X^7$-Ser-Asp-$X^{10}$-$X^{11}$-Lys-Gln-

Met-Glu-Glu-Glu-Ala.

14. The peptide derivative of claim 10, wherein the peptide is selected from the group consisting of:

SEQ ID No. 12:
His-Gly-Glu-Gly-Thr-$X^6$-$X^7$-Ser-Asp-Leu-Ser-Lys-Gln-

Met-Glu-Glu-Glu-Ala;
and

SEQ ID No. 13:
His-Gly-Glu-Gly-Thr-Phe-Thr-Ser-Asp-$X^{10}$-$X^{11}$-Lys-

Gln-Met-Glu-Glu-Glu-Ala.

15. The peptide derivative of claim 10, wherein the peptide has the sequence:

SEQ ID No. 4:
His-Gly-Glu-Gly-Thr-$X^6$-$X^7$-Ser-Asp-$X^{10}$-$X^{11}$-Lys-Gln-

Met-Glu-Glu-Glu-Ala-Val.

16. The peptide derivative fragment of claim 10, wherein the fragment peptide is selected from the group consisting of:

SEQ ID No. 2:
His-Gly-Glu-Gly-Thr-$X^6$-$X^7$-Ser-Asp-Leu-Ser-Lys-Gln-

Met-Glu-Glu-Glu-Ala-Val;
and

SEQ ID No. 3:
His-Gly-Glu-Gly-Thr-Phe-Thr-Ser-Asp-$X^{10}$-$X^{11}$-Lys-

Gln-Met-Glu-Glu-Glu-Ala-Val.

17. A method of making a protected derivative of an insulinotropic peptide, comprising the steps of:
 a) preparing a first protected peptide fragment including an amino acid sequence comprising at least two repeating glutamates in direct sequence (Glu-Glu) and further comprising a pseudoproline moiety; and
 b) assembling by solution phase coupling the first protected peptide fragment with at least a second protected peptide and generating a protected derivative of an insulinotropic peptide.

18. The method of claim 17, wherein at least a first pseudoproline moiety is between the repeating sequence of glutamic acid residues and the N-terminus of the first protected peptide fragment.

19. The method of claim 18, wherein there are at least two amino acid residues between the first pseudoproline moiety and the closest Glu residue of the repeating sequence of glutamic acid residues of the first protected peptide fragment.

20. The method of claim 18, the protected derivative further comprising a second pseudoproline moiety downstream from the first pseudoproline moiety.

21. The method of claim 17, wherein the protected derivative comprises at least 15 amino acid residues.

22. The method of claim 21, wherein the protected derivative comprises up to 21 amino acid residues.

23. The method of claim 17, wherein no more than two amino acid residues are between the repeating sequence of glutamic acid residues and the C-terminus of the protected derivative.

24. The method of claim 17, wherein the repeating glutamic acid residues are the C-terminus of the protected derivative.

25. The method of claim 17, wherein the protected derivative is comprised of at least three consecutive glutamic acid residues (Glu-Glu-Glu).

26. The method of claim 17, wherein the protected derivative is selected from the group consisting of:

SEQ ID No. 2:
His-Gly-Glu-Gly-Thr-$X^6$-$X^7$-Ser-Asp-Leu-Ser-Lys-Gln-

Met-Glu-Glu-Glu-Ala-Val;

SEQ ID No. 3:
His-Gly-Glu-Gly-Thr-Phe-Thr-Ser-Asp-$X^{10}$-$X^{11}$-Lys-

Gln-Met-Glu-Glu-Glu-Ala-Val;

SEQ ID No. 4:
His-Gly-Glu-Gly-Thr-$X^6$-$X^7$-Ser-Asp-$X^{10}$-$X^{11}$-Lys-Gln-

Met-Glu-Glu-Glu-Ala-Val;

SEQ ID No. 5:
His-Gly-Glu-$X^4$-$X^5$-Phe-Thr-Ser-Asp-Leu-Ser-Lys-Gln-

Met-Glu-Glu-Glu-Ala-Val;

SEQ ID No. 6:
His-Gly-Glu-$X^4$-$X^5$-Phe-Thr-Ser-Asp-$X^{10}$-$X^{11}$-Lys-Gln-

Met-Glu-Glu-Glu-Ala-Val;

SEQ ID No. 7:
His-Gly-Glu-$X^4$-$X^5$-Phe-$X^7$-$X^8$-Asp-Leu-Ser-Lys-Gln-

Met-Glu-Glu-Glu-Ala-Val;

SEQ ID No. 8:
His-Gly-Glu-$X^4$-$X^5$-$X^6$-$X^7$-Ser-Asp-Leu-Ser-Lys-Gln-

Met-Glu-Glu-Glu-Ala-Val;

SEQ ID No. 9:
His-Gly-Glu-Gly-Thr-Phe-$X^7$-$X^8$-Asp-Leu-Ser-Lys-Gln-

Met-Glu-Glu-Glu-Ala-Val;

SEQ ID No. 10:
His-Gly-Glu-Gly-Thr-Phe-$X^7$-$X^8$-Asp-$X^{10}$-$X^{11}$-Lys-Gln-

Met-Glu-Glu-Glu-Ala-Val;

SEQ ID No. 11:
His-Gly-Glu-$X^4$-$X^5$-Phe-$X^7$-$X^8$-Asp-$X^{10}$-$X^{11}$-Lys-Gln-

Met-Glu-Glu-Glu-Ala-Val;

SEQ ID No. 12:
His-Gly-Glu-Gly-Thr-$X^6$-$X^7$-Ser-Asp-Leu-Ser-Lys-Gln-

Met-Glu-Glu-Glu-Ala;

SEQ ID No. 13:
His-Gly-Glu-Gly-Thr-Phe-Thr-Ser-Asp-$X^{10}$-$X^{11}$-Lys-

Gln-Met-Glu-Glu-Glu-Ala;

SEQ ID No. 14:
His-Gly-Glu-Gly-Thr-$X^6$-$X^7$-Ser-Asp-$X^{10}$-$X^{11}$-Lys-Gln-

Met-Glu-Glu-Glu-Ala;

SEQ ID No. 15:
His-Gly-Glu-$X^4$-$X^5$-Phe-Thr-Ser-Asp-Leu-Ser-Lys-Gln-

Met-Glu-Glu-Glu-Ala;

SEQ ID No. 16:
His-Gly-Glu-$X^4$-$X^5$-Phe-Thr-Ser-Asp-$X^{10}$-$X^{11}$-Lys-Gln-

Met-Glu-Glu-Glu-Ala;

SEQ ID No. 17:
His-Gly-Glu-$X^4$-$X^5$-Phe-$X^7$-$X^8$-Asp-Leu-Ser-Lys-Gln-

Met-Glu-Glu-Glu-Ala;

SEQ ID No. 18:
His-Gly-Glu-$X^4$-$X^5$-$X^6$-$X^7$-Ser-Asp-Leu-Ser-Lys-Gln-

Met-Glu-Glu-Glu-Ala;

SEQ ID No. 19:
His-Gly-Glu-Gly-Thr-Phe-$X^7$-$X^8$-Asp-Leu-Ser-Lys-Gln-

Met-Glu-Glu-Glu-Ala;

-continued

SEQ ID No. 20:
His-Gly-Glu-Gly-Thr-Phe-$X^7$-$X^8$-Asp-$X^{10}$-$X^{11}$-Lys-Gln-

Met-Glu-Glu-Glu-Ala;

SEQ ID No. 21:
His-Gly-Glu-$X^4$-$X^5$-Phe-$X^7$-$X^8$-Asp-$X^{10}$-$X^{11}$-Lys-Gln-

Met-Glu-Glu-Glu-Ala;

SEQ ID No. 22:
His-Gly-Glu-Gly-Thr-$X^6$-$X^7$-Ser-Asp-Leu-Ser-Lys-Gln-

Met-Glu-Glu-Glu;

SEQ ID No. 23:
His-Gly-Glu-Gly-Thr-Phe-Thr-Ser-Asp-$X^{10}$-$X^{11}$-Lys-

Gln-Met-Glu-Glu-Glu;

SEQ ID No. 24:
His-Gly-Glu-Gly-Thr-$X^6$-$X^7$-Ser-Asp-$X^{10}$-$X^{11}$-Lys-Gln-

Met-Glu-Glu-Glu;

SEQ ID No. 25:
His-Gly-Glu-$X^4$-$X^5$-Phe-Thr-Ser-Asp-Leu-Ser-Lys-Gln-

Met-Glu-Glu-Glu;

SEQ ID No. 26:
His-Gly-Glu-$X^4$-$X^5$-Phe-Thr-Ser-Asp-$X^{10}$-$X^{11}$-Lys-Gln-

Met-Glu-Glu-Glu;

SEQ ID No. 27:
His-Gly-Glu-$X^4$-$X^5$-Phe-$X^7$-$X^8$-Asp-Leu-Ser-Lys-Gln-

Met-Glu-Glu-Glu;

SEQ ID No. 28:
His-Gly-Glu-$X^4$-$X^5$-$X^6$-$X^7$-Ser-Asp-Leu-Ser-Lys-Gln-

Met-Glu-Glu-Glu;

SEQ ID No. 29:
His-Gly-Glu-Gly-Thr-Phe-$X^7$-$X^8$-Asp-Leu-Ser-Lys-Gln-

Met-Glu-Glu-Glu;

SEQ ID No. 30:
His-Gly-Glu-Gly-Thr-Phe-$X^7$-$X^8$-Asp-$X^{10}$-$X^{11}$-Lys-Gln-

Met-Glu-Glu-Glu;
and

SEQ ID No. 31:
His-Gly-Glu-$X^4$-$X^5$-Phe-$X^7$-$X^8$-Asp-$X^{10}$-$X^{11}$-Lys-Gln-

Met-Glu-Glu-Glu;

wherein in SEQ ID Nos. 2 through 31 $X^4$-$X^5$ at positions 4 and 5; $X^6$-$X^7$ at positions 6 and 7; $X^7$-$X^8$ at positions 7 and 8; and $X^{10}$-$X^{11}$ at positions 10 and 11 comprise to a pseudoproline.

27. The method of claim 26, wherein the protected derivative has the sequence:

SEQ ID No. 24:
His-Gly-Glu-Gly-Thr-$X^6$-$X^7$-Ser-Asp-$X^{10}$-$X^{11}$-Lys-Gln-

Met-Glu-Glu-Glu.

28. The method of claim 26, wherein the protected derivative is selected from the group consisting of:

SEQ ID No. 22:
His-Gly-Glu-Gly-Thr-$X^6$-$X^7$-Ser-Asp-Leu-Ser-Lys-Gln-

Met-Glu-Glu-Glu;
and

SEQ ID No. 23:
His-Gly-Glu-Gly-Thr-Phe-Thr-Ser-Asp-$X^{10}$-$X^{11}$-Lys-Gln-

Met-Glu-Glu-Glu.

29. The method of claim 26, wherein the protected derivative has the sequence:

SEQ ID No. 14:
His-Gly-Glu-Gly-Thr-$X^6$-$X^7$-Ser-Asp-$X^{10}$-$X^{11}$-Lys-Gln-

Met-Glu-Glu-Glu-Ala.

30. The method of claim 26, wherein the protected derivative is selected from the consisting of:

SEQ ID No. 12:
His-Gly-Glu-Gly-Thr-$X^6$-$X^7$-Ser-Asp-Leu-Ser-Lys-Gln-

Met-Glu-Glu-Glu-Ala;
and

SEQ ID No. 13:
His-Gly-Glu-Gly-Thr-Phe-Thr-Ser-Asp-$X^{10}$-$X^{11}$-Lys-

Gln-Met-Glu-Glu-Glu-Ala.

31. The method of claim 26, wherein the protected derivative has the sequence:

SEQ ID No. 4:
His-Gly-Glu-Gly-Thr-$X^6$-$X^7$-Ser-Asp-$X^{10}$-$X^{11}$-Lys-Gln-

Met-Glu-Glu-Glu-Ala-Val.

32. The method of claim 26, wherein the protected derivative is selected from the group consisting of:

SEQ ID No. 2:
His-Gly-Glu-Gly-Thr-$X^6$-$X^7$-Ser-Asp-Leu-Ser-Lys-Gln-

Met-Glu-Glu-Glu-Ala-Val;
and

SEQ ID No. 3:
His-Gly-Glu-Gly-Thr-Phe-Thr-Ser-Asp-$X^{10}$-$X^{11}$-Lys-

Gln-Met-Glu-GIu-Glu-Ala-Val.

33. The peptide derivative of claim 2, wherein the sequence of repeating Glu residues includes at least three consecutive Glu residues.

34. The peptide derivative of claim 2, wherein at least 8 amino acid residues are between the repeating Glu residues and the N-terminus of the protected derivative.

35. The peptide derivative of claim 2, wherein the peptide comprises at least an amino acid sequence according to any of SEQ ID Nos. 2 through_31, 35 through 39 or 50 through 59.

36. The peptide derivative according to claim 2, wherein the protected derivative comprises at least an amino acid sequence according to any of SEQ ID Nos. 2 through 31.

37. The peptide derivative according to claim 2, wherein the protected derivative comprises at least an amino acid sequence according to any of SEQ ID Nos. 2, 3, 4, 12, 13, 14, 22, 23, and 24.

38. A peptide derivative consisting of an amino acid sequence selected from the group consisting of SEQ ID Nos. 35-39.

39. A peptide derivative consisting of an amino acid sequence selected from the group consisting of SEQ ID Nos. 40-42.

40. A method of making a protected peptide derivative, which when deprotected has insulinotropic activity, comprising the steps of:
   a) providing first, second, and third protected peptides, said first protected peptide comprising a sequence of at least two repeating Glu residues (Glu-Glu) and at least one residue of a pseudoproline, and comprising at least one protecting group on any of the first, second and third protected peptides;
   b) coupling a Serine residue to the third protected peptide to obtain a fourth protected peptide;
   c) coupling the fourth protected peptide to the second protected peptide to obtain a fifth protected peptide; and
   d) coupling the fifth protected peptide to the first protected peptide to generates the protected peptide derivative, which when deprotected has insulinotropic activity.

41. The method of claim 40, further comprising the steps of:
   e) deprotecting the protected peptide derivative and chromatographically purifying the deprotected peptide derivative having insulinotropic activity; and
   f) precipitating the purified insulinotropic peptide out of solution.

42. The method of claim 41, wherein step f) further comprises using at least ethanol for precipitating the purified insulinotropic peptide.

43. The method of claim 40, further comprising synthesizing the first, the second, and the third protected peptides using solid phase synthesis techniques.

44. The method of claim 40, further comprising performing b), c) and d) in solution phase.

45. The method of claim 40 wherein at least a first pseudoproline moiety is between the repeating sequence of glutamic acid residues and the N-terminus of the first protected peptide.

46. The method of claim 45 wherein there are at least two amino acid residues between the first pseudoproline moiety and the closest Glu residue of the repeating sequence of glutamic acid residues.

47. The method of claim 45, wherein the method comprises introducing to the first protected peptide, a second pseudoproline moiety downstream from the first pseudoproline moiety.

48. The method of claim 40 wherein the first protected peptide comprises at least 15 amino acid residues.

49. The method of claim 40, wherein the first protected peptide comprises up to 21 amino acid residues.

50. The method of claim 40, wherein no more than two amino acid residues are between the repeating sequence of glutamic acid residues and the C-terminus of the first protected peptide.

51. The method of claim 40, wherein the repeating glutamic acid residues are the C-terminus of the first protected peptide.

52. The method of claim 40 wherein the first protected peptide comprises at least three consecutive glutamic acid residues (Glu-Glu-Glu).

53. The method of claim 40, wherein the first protected peptide has an amino acid sequence according to any of SEQ ID Nos. 2, 3, 4, 12, 13, 14, 22, 23, and 24.

54. The method of claim 40, wherein the second protected peptide has an amino acid sequence according to any of SEQ ID Nos. 35-39.

55. The method of claim 40, wherein the third protected peptide has an amino acid sequence according to any of SEQ ID Nos. 40-42.

* * * * *